(12) United States Patent
Namai et al.

(10) Patent No.: US 9,720,322 B2
(45) Date of Patent: Aug. 1, 2017

(54) PHOTORESIST COMPOSITION, COMPOUND, AND PRODUCTION METHOD THEREOF

(71) Applicant: JSR CORPORATION, Tokyo (JP)

(72) Inventors: Hayato Namai, Tokyo (JP); Norihiko Ikeda, Tokyo (JP); Takanori Kawakami, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 15/252,553

(22) Filed: Aug. 31, 2016

(65) Prior Publication Data

US 2016/0370700 A1 Dec. 22, 2016

Related U.S. Application Data

(63) Continuation of application No. 14/491,286, filed on Sep. 19, 2014, now Pat. No. 9,477,149, which is a
(Continued)

(30) Foreign Application Priority Data

Mar. 19, 2012 (JP) ................................. 2012-062856
Aug. 16, 2012 (JP) ................................. 2012-180604

(51) Int. Cl.
*G03F 7/004* (2006.01)
*C07C 381/12* (2006.01)
(Continued)

(52) U.S. Cl.
CPC .......... *G03F 7/0045* (2013.01); *C07C 309/17* (2013.01); *C07C 309/18* (2013.01); *C07C 309/27* (2013.01); *C07C 381/12* (2013.01); *C07D 207/416* (2013.01); *C07D 211/46* (2013.01); *C07D 237/04* (2013.01); *C07D 237/16* (2013.01); *C07D 295/18* (2013.01); *C07D 295/185* (2013.01); *C07D 307/33* (2013.01); *C07D 307/60* (2013.01); *C07D 307/64* (2013.01); *C07D 307/93* (2013.01); *C07D 307/94* (2013.01); *C07D 311/20* (2013.01); *C07D 311/74* (2013.01); *C07D 313/06* (2013.01); *C07D 317/24* (2013.01); *C07D 319/06* (2013.01); *C07D 321/12* (2013.01); *C07D 327/04* (2013.01); *C07D 493/10* (2013.01); *G03F 7/0046* (2013.01);
(Continued)

(58) Field of Classification Search
CPC ... C07C 309/02; C07C 309/07; C07C 309/13; C07C 309/14; C07C 309/19; C07C 309/21; C07C 381/12; C07C 309/17; G03F 7/027; G03F 7/038; G03F 7/039
See application file for complete search history.

(56) References Cited

U.S. PATENT DOCUMENTS 4,013,445 A * 3/1977 Bellus .................. C07F 7/1896
 504/164
4,491,628 A 1/1985 Ito et al.
(Continued)

FOREIGN PATENT DOCUMENTS

| | | |
|---|---|---|
| JP | 59-45439 | 3/1984 |
| JP | 10-010715 | 1/1998 |
| JP | 2007-106717 | 4/2007 |
| JP | 2010-111653 | 5/2010 |
| JP | 2011-138060 A1 | 7/2011 |
| WO | WO 2011/030737 | 3/2011 |
| WO | WO 2012/020627 A1 | 2/2012 |

OTHER PUBLICATIONS

Alves de Sousa, R., Artaud, I-Bis-b-sulfanylethylester and cyclic disulfide-S-oxides as precursors of bifunctionalized anionic derivatives with two oxidized sulfurs, Tetrahedron, 64 (2008), pp. 2198-2206.*

(Continued)

*Primary Examiner* — Anca Eoff
(74) *Attorney, Agent, or Firm* — Oblon, McClelland, Maier & Neustadt, L.L.P.

(57) ABSTRACT

A photoresist composition containing (A) a polymer having a structural unit (I) that includes an acid-labile group, and (I) a compound represented by the following formula (1). In the following formula (1), $R^1$, $R^2$, $R^3$ and R represent a hydrogen atom or a monovalent organic group having 1 to 20 carbon atoms. X represents a single bond, an oxygen atom or —$NR^a$—. $R^a$ represents a hydrogen atom, a hydroxy group or a monovalent organic group having 1 to 20 carbon atoms, and optionally taken together represents a ring structure by binding with R each other. $A^-$ represents —$SO_3^-$ or —$CO_2^-$. $M^+$ represents a monovalent onium cation.

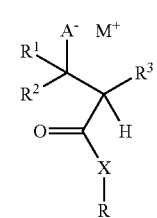

(1)

14 Claims, No Drawings

Related U.S. Application Data continuation of application No. PCT/JP2013/055258, filed on Feb. 27, 2013.

(51) Int. Cl.

| | | |
|---|---|---|
| *C07D 307/93* | (2006.01) | |
| *C07D 307/94* | (2006.01) | |
| *C07D 311/74* | (2006.01) | |
| *C07D 313/06* | (2006.01) | |
| *C07D 317/24* | (2006.01) | |
| *C07D 319/06* | (2006.01) | |
| *C07D 321/12* | (2006.01) | |
| *C07D 327/04* | (2006.01) | |
| *C07C 309/17* | (2006.01) | |
| *C07D 237/04* | (2006.01) | |
| *C07D 237/16* | (2006.01) | |
| *C07D 493/10* | (2006.01) | |
| *C07D 207/416* | (2006.01) | |
| *C07D 211/46* | (2006.01) | |
| *C07D 295/18* | (2006.01) | |
| *C07D 307/33* | (2006.01) | |
| *C07D 307/64* | (2006.01) | |
| *C07C 309/27* | (2006.01) | |
| *G03F 7/039* | (2006.01) | |
| *G03F 7/11* | (2006.01) | |
| *G03F 7/20* | (2006.01) | |
| *G03F 7/027* | (2006.01) | |
| *G03F 7/038* | (2006.01) | |
| *C07C 309/18* | (2006.01) | |
| *C07D 295/185* | (2006.01) | |
| *C07D 307/60* | (2006.01) | |
| *C07D 311/20* | (2006.01) | |

(52) U.S. Cl.
CPC .............. *G03F 7/027* (2013.01); *G03F 7/038* (2013.01); *G03F 7/039* (2013.01); *G03F 7/0388* (2013.01); *G03F 7/0392* (2013.01); *G03F 7/0397* (2013.01); *G03F 7/11* (2013.01); *G03F 7/2041* (2013.01); *C07C 2101/08* (2013.01); *C07C 2101/10* (2013.01); *C07C 2101/14* (2013.01); *C07C 2101/18* (2013.01); *C07C 2103/74* (2013.01)

(56) References Cited

U.S. PATENT DOCUMENTS

| | | |
|---|---|---|
| 7,414,148 B2 | 8/2008 | Fujiwara et al. |
| 2006/0210922 A1* | 9/2006 | Nishiyama ............ G03F 7/0045 430/270.1 |
| 2009/0142851 A1 | 6/2009 | Shima et al. |
| 2011/0201823 A1 | 8/2011 | Yoshida et al. |
| 2011/0287361 A1 | 11/2011 | Bae et al. |
| 2012/0164582 A1 | 6/2012 | Maruyama |

OTHER PUBLICATIONS

International Search Report issued May 21, 2013 in PCT/JP2013/055258 filed Feb. 27, 2013.
Office Action issued May 10, 2016, in Japanese Patent Application No. 2014-506104 (w/ English translation).
Office Action issued Jul. 27, 2016, in Taiwan Patent Application No. 102109630 filed Mar. 19, 2013 (w/ English translation).
Machine translation of JP 10-010715, published on Jan. 16, 1998.
Machine translation of JP 2010-111653, published on May 20, 2010.
Machine translation of JP 2011-138060, published on Jul. 14, 2011.
Office Action issued Dec. 27, 2016, in Taiwanese Patent Application No. 102109630 filed Mar. 19, 2013 (w/ English translation).

* cited by examiner

PHOTORESIST COMPOSITION, COMPOUND, AND PRODUCTION METHOD THEREOF

CROSS-REFERENCE TO RELATED APPLICATIONS

The present application is a continuation application of U.S. patent application Ser. No. 14/491,286 filed Sep. 19, 2014, which in turn is a continuation application of International Application No. PCT/JP2013/055258, filed Feb. 27, 2013, which claims priority to Japanese Patent Application No. 2012-062856, filed Mar. 19, 2012, and to Japanese Patent Application No. 2012-180604, filed Aug. 16, 2012. The contents of these applications are incorporated herein by reference in their entirety.

TECHNICAL FIELD

The present invention relates to a photoresist composition, a compound and a production method thereof.

BACKGROUND ART

In the field of microfabrication typified by production of integrated circuit devices, fine resist patterns have been conventionally formed by: providing a resist film on a substrate using a photoresist composition containing a polymer having an acid-labile group; exposing the resist film by irradiating with a radioactive ray having a short wavelength such as an excimer laser beam through a mask pattern; and eliminating a light-exposed site with an alkaline developer solution. In this process, a "chemically amplified resist" in which an acid generating agent that generates an acid upon irradiation with a radioactive ray is contained in the photoresist composition to enhance the sensitivity by the action of the acid is used (see Japanese Unexamined Patent Application, Publication No. S59-45439).

As the photoresist composition for use in such chemically amplified resists, a composition containing an acid diffusion control agent together with the acid generating agent so as to enable a fine resist pattern to be formed has been disclosed (see Japanese Unexamined Patent Application, Publication No. 2007-106717). According to such a photoresist composition, inhibition of the diffusion of an acid generated from the acid generating agent by the acid diffusion control agent reportedly enables a contrast between a light-exposed site and a light-unexposed site to be improved.

However, even in the case in which the acid generating agent and the acid diffusion control agent as disclosed above are used, resulting from diffusion and the like of these acid generating agent and acid diffusion control agent per se, characteristics such as an LWR (Line Width Roughness) performance, a resolution and a cross-sectional shape of the resist pattern formed still remain insufficient.

PRIOR ART DOCUMENTS

Patent Documents

Patent Document 1: Japanese Unexamined Patent Application, Publication No. S59-45439
Patent Document 2: Japanese Unexamined Patent Application, Publication No. 2007-106717

SUMMARY OF THE INVENTION

Problems to be Solved by the Invention

The present invention was made in view of the foregoing circumstances, and an object of the invention is to provide: a photoresist composition capable of improving characteristic features such as an LWR performance, a resolution and a cross-sectional shape; a compound suitable as a basic ingredient of the photoresist composition; and a production method thereof.

Means for Solving the Problems

According to an aspect of the invention made for solving the aforementioned problems, a photoresist composition is provided which contains:

(A) a polymer having (I) a structural unit that includes an acid-labile group (hereinafter, may be also referred to as "(A) polymer" or "polymer (A)"); and (I) a compound represented by the following formula (1).

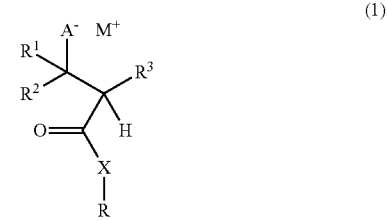

In the formula (1), $R^1$, $R^2$, $R^3$ and R each independently represent a hydrogen atom or a monovalent organic group having 1 to 20 carbon atoms, wherein two of $R^1$, $R^2$, $R^3$ and R optionally taken together represent a ring structure by binding with each other; and X represents a single bond, an oxygen atom or —$NR^a$—, wherein $R^a$ represents a hydrogen atom, a hydroxy group or a monovalent organic group having 1 to 20 carbon atoms, and optionally taken together represents a ring structure by binding with R each other; and $A^-$ represents —$SO_3^-$ or —$CO_2^-$; and $M^+$ represents a monovalent onium cation, wherein, in a case where $A^-$ represents —$CO_2^-$, at least one of $R^1$, $R^2$, $R^3$ and R does not represent a hydrogen atom.

Due to containing the compound (I) in the photoresist composition, the compound (I) serves as an acid diffusion control agent and/or an acid generating agent (hereinafter, may be also referred to as "acid diffusion control agent, etc."), and thus diffusion of the acid diffusion control agent, etc., in the resist film formed can be inhibited, leading to an improvement of a contrast between a light-exposed site and a light-unexposed site to enable a resist pattern superior in characteristics such as an LWR performance to be formed.

It is preferred that the compound (I) represented by the above formula (1) is any one of compounds represented by the following formulae (1-1-1) to (1-1-5), or a mixture of these compounds.

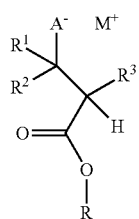
(1-1-1)

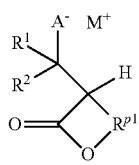
(1-1-2)

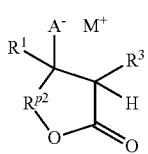
(1-1-3)

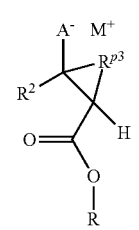
(1-1-4)

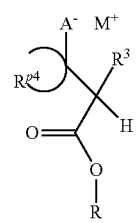
(1-1-5)

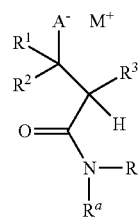
(1-2-1)

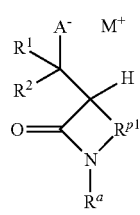
(1-2-2)

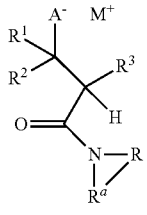
(1-2-3)

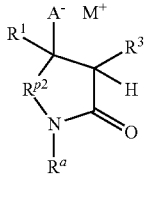
(1-2-4)

In the formulae (1-1-1) to (1-1-5), $M^+$, $A^-$, $R^1$, $R^2$, $R^3$ and R are as defined in the above formula (1); and $R^{p1}$, $R^{p2}$, $R^{p3}$ and $R^{p4}$ each independently represent a divalent organic group.

When the compound (I) represented by the above formula (1) is represented by one of the above specific formulae, the diffusion of the acid diffusion control agent, etc., in the resist film formed can be further inhibited according to the photoresist composition, leading to an improvement of a contrast between a light-exposed site and a light-unexposed site to enable a resist pattern more superior in characteristics such as an LWR performance to be formed.

It is also preferred that the compound (I) represented by the above formula (1) is any one of compounds represented by the following formulae (1-2-1) to (1-2-4), or a mixture of these compounds.

In the formulae (1-2-1) to (1-2-4), $M^+$, $A^-$, $R^1$, $R^2$, $R^3$, R and $R^a$ are as defined in the above formula (1); and $R^{p1}$ and $R^{p2}$ each independently represent a divalent organic group.

When the compound (I) represented by the above formula (1) is represented by one of the above specific formulae, the diffusion of the acid diffusion control agent, etc., in the resist film formed can be further inhibited according to the photoresist composition, leading to an improvement of a contrast between a light-exposed site and a light-unexposed site to enable a resist pattern more superior in characteristics such as an LWR performance to be formed.

It is also preferred that the compound (I) represented by the above formula (1) is represented by the following formula (2).

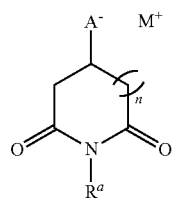
(2)

In the formula (2), $A^-$, $M^+$ and $R^a$ are as defined in the above formula (1); and n is an integer of 0 to 5.

When the compound (I) represented by the above formula (1) is represented by the above formula (2), the diffusion of the acid diffusion control agent, etc., in the resist film formed can be further inhibited according to the photoresist composition, leading to an improvement of a contrast between a light-exposed site and a light-unexposed site to enable a resist pattern more superior in characteristics such as an LWR performance to be formed.

It is preferred that the photoresist composition further contains (B) an acid diffusion control agent, and the acid diffusion control agent (B) includes the compound (I) (hereinafter, the "photoresist composition containing the acid diffusion control agent (B)" may be also referred to as "photoresist composition (I)").

When the photoresist composition contains the acid diffusion control agent (B), diffusion of the acid diffusion control agent (B) per se can be inhibited, consequently leading to an improvement of a contrast between a light-exposed site and a light-unexposed site to enable a resist pattern superior in characteristics such as an LWR performance to be formed.

It is preferred that the acid-labile group in the structural unit (I) is polar, or the polymer (A) further has (II) a structural unit represented by the following formula (3).

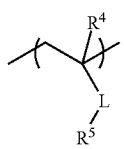
(3)

In the formula (3), $R^4$ represents a hydrogen atom, a fluorine atom, a methyl group or a trifluoromethyl group; L represents a single bond, —CO—O— or —CO—NH—; and $R^5$ represents an acid-nonlabile and polar group.

When the acid-labile group in the structural unit (I) is polar, or the polymer (A) further has the above specific structural unit, a uniform resist film can be formed.

It is preferred that the photoresist composition further contains (C) an acid generating agent, and the acid generating agent (C) differs from the compound (I). When the photoresist composition further contains the above specific acid generating agent, the sensitivity can be enhanced, and consequently the contrast of the resist pattern formed can be improved.

It is also preferred that the photoresist composition contains (D) an acid generating agent, and the acid generating agent (D) includes the compound (I) (hereinafter, the "photoresist composition containing the acid generating agent (D)" may be also referred to as "photoresist composition (II)").

When the photoresist composition contains the acid generating agent (D), diffusion of the acid generating agent (D) per se can be inhibited, consequently leading to an improvement of a contrast between a light-exposed site and a light-unexposed site to enable a resist pattern superior in characteristics such as an LWR performance to be formed.

It is preferred that the photoresist composition further contains (E) an acid diffusion control agent, and the acid diffusion control agent (E) differs from the compound (I). When the photoresist composition further contains the above specific acid diffusion control agent, diffusion of an acid generated upon an exposure can be inhibited, and consequently the contrast of the resist pattern formed can be improved.

According to another aspect of the invention made for solving the aforementioned problems, a compound represented by the following formula (1) is provided.

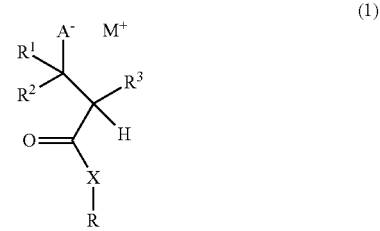
(1)

In the formula (1), $R^1$, $R^2$, $R^3$ and R each independently represent a hydrogen atom or a monovalent organic group having 1 to 20 carbon atoms, wherein two of $R^1$, $R^2$, $R^3$ and R optionally taken together represent a ring structure by binding with each other; and X represents a single bond, an oxygen atom or —$NR^a$—, wherein $R^a$ represents a hydrogen atom, a hydroxy group or a monovalent organic group having 1 to 20 carbon atoms, and optionally taken together represents a ring structure by binding with R each other; and $A^-$ represents —$SO_3^-$ or —$CO_2^-$; and $M^+$ represents a monovalent onium cation, wherein in a case where $A^-$ represents —$CO_2^-$, at least one of $R^1$, $R^2$, $R^3$ and R does not represent a hydrogen atom.

Due to having the above specific structure, when the compound is used as an acid diffusion control agent, etc., for a photoresist composition, diffusion of the acid diffusion control agent, etc., in the resist film formed can be inhibited, leading to an improvement of a contrast between a light-exposed site and a light-unexposed site to enable a resist pattern superior in characteristics such as an LWR performance to be formed.

It is preferred that X in the above formula (1) represents an oxygen atom, and R represents an acid-nonlabile group represented by the following formula (i).

(i)

In the formula (i), $R^{b1}$, $R^{b2}$ and $R^{b3}$ each independently represent a hydrogen atom, a hydroxy group or a monovalent organic group having 1 to 19 carbon atoms, wherein at least one of the organic group includes at least one of a polar group and a linking group, and the linking group is —O—CO—O—, —S—, —O—, —$SO_2$—O—, —NH— or —CO—O—, and wherein two or more of $R^{b1}$, $R^{b2}$ and $R^{b3}$ optionally taken together represent a ring structure by binding with each other, and at least one of $R^{b1}$, $R^{b2}$ and $R^{b3}$ does not represent a hydrogen atom.

When the compound has the above specific structure, the photoresist composition containing the compound as an acid diffusion control agent, etc., enables a resist pattern more superior in characteristics such as an LWR performance to be formed. This event is presumed to result from improved compatibility owing to a similarity of the structure of the compound to the structure of a polymer usually contained in the photoresist composition, consequently leading to formation of a uniform resist film.

It is also preferred that X in the above formula (1) represents an oxygen atom, and R represents an acid-labile group represented by the following formula (ii).

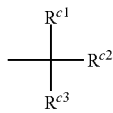

(ii)

In the formula (ii), $R^{c1}$, $R^{c2}$ and $R^{c3}$ each independently represent an alkyl group having 1 to 19 carbon atoms or a monovalent alicyclic hydrocarbon group having 3 to 19 carbon atoms, wherein a part or all of hydrogen atoms included in the alkyl group and the alicyclic hydrocarbon group are unsubstituted or substituted, and wherein two of $R^{c1}$, $R^{c2}$ and $R^{c3}$ optionally taken together represent a divalent alicyclic hydrocarbon group having 3 to 20 carbon atoms by binding with each other together with the carbon atom to which the two of $R^{c1}$, $R^{c2}$ and $R^{c3}$ bond.

When the compound has the above specific structure, according to the photoresist composition containing the compound as an acid diffusion control agent, etc., the difference in a rate of dissolution between the light-exposed site and the light-unexposed site can be increased owing to dissociation of the acid-labile group upon an exposure, and as a result, formation of a resist pattern more superior in characteristics such as an LWR performance is enabled.

It is also preferred that the compound (I) represented by the above formula (1) is represented by the following formula (2).

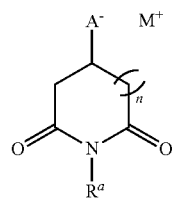

(2)

In the formula (2), $A^-$, $M^+$ and $R^a$ are as defined in the above formula (1); and n is an integer of 0 to 5.

When the compound has the above specific structure, according to the photoresist composition containing the compound as an acid diffusion control agent, etc., the diffusion of the acid diffusion control agent, etc., in the resist film formed can be further inhibited, leading to an improvement of a contrast between a light-exposed site and a light-unexposed site to enable a resist pattern more superior in characteristics such as an LWR performance to be formed.

It is preferred that the compound is used as an acid diffusion control agent or an acid generating agent. When the compound is used as the acid diffusion control agent and/or the acid generating agent, a resist pattern superior in characteristics such as an LWR performance can be formed according to the photoresist composition containing the compound.

According to yet another aspect of the present invention made for solving the aforementioned problems, a method for producing a compound represented by the following formula (6) is provided, the method including:

(1) allowing a compound represented by the following formula (4) to react with NaHSO$_3$; and (2) allowing a compound obtained in the step (1) to react with a compound represented by the following formula (5).

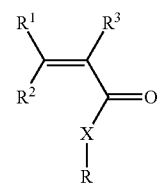

(4)

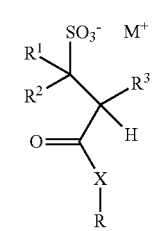

(5)

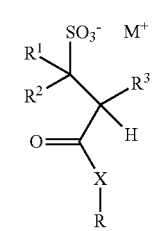

(6)

In the formulae (4) and (6), $R^1$, $R^2$, $R^3$ and R each independently represent a hydrogen atom or a monovalent organic group having 1 to 20 carbon atoms, wherein two of $R^1$, $R^2$, $R^3$ and R optionally taken together represent a ring structure by binding with each other; and X represents a single bond, an oxygen atom or —$NR^a$—, wherein $R^a$ represents a hydrogen atom, a hydroxy group or a monovalent organic group having 1 to 20 carbon atoms, and optionally taken together represents a ring structure by binding with R each other.

In the formulae (5) and (6), $M^+$ represents a monovalent onium cation.

In the formula (5), $E^-$ represents a monovalent anion.

Due to having the above specific steps, the production method enables the compound to be readily and certainly produced.

It is to be noted that the term, "organic group" as referred to means a group that includes at least one carbon atom.

Effects of the Invention

According to the photoresist composition of the aspect of the present invention, a contrast between a light-exposed site and a light-unexposed site is improved to enable a resist pattern superior in characteristics such as an LWR performance to be formed. Therefore, the photoresist composition, a compound suited as a basic ingredient of the photoresist composition, and a production method thereof can be suitably used in processes for producing a semiconductor device in which further miniaturization of patterns has been further in progress.

DESCRIPTION OF EMBODIMENTS

Photoresist Composition

The photoresist composition according to an embodiment of the present invention contains (A) a polymer and (I) a compound. In addition, the photoresist composition may contain optional component(s) other than the polymer (A) and the compound (I) within a range not leading to impairment of the effects of the present invention. Hereinafter, each component will be explained.

(A) Polymer

The polymer (A) has (I) a structural unit that includes an acid-labile group. The polymer (A) is similar to the polymer (A) in (I) a photoresist composition described later. With respect to the polymer (A), it is to be noted that since the explanation of the polymer (A) in (I) Photoresist Composition can be applied thereto, detailed explanation in this section is omitted.

(I) Compound

The compound (I) is represented by the above formula (1). Due to having the above structure, the compound (I) can inhibit diffusion in the resist film formed, leading to an improvement of a contrast between a light-exposed site and a light-unexposed site to enable a resist pattern superior in characteristics such as an LWR performance to be formed. The compound (I) will be described in detail below.

In the above formula (1), $R^1$, $R^2$, $R^3$ and R each independently represent a hydrogen atom or a monovalent organic group having 1 to 20 carbon atoms, wherein two of $R^1$, $R^2$, $R^3$ and R optionally taken together represent a ring structure by binding with each other; X represents a single bond, an oxygen atom or —$NR^a$—, wherein $R^a$ represents a hydrogen atom, a hydroxy group or a monovalent organic group having 1 to 20 carbon atoms, and optionally taken together represents a ring structure by binding with R each other; $A^-$ represents —$SO_3^-$ or —$CO_2^-$, and $M^+$ represents a monovalent onium cation, wherein in a case where $A^-$ represents —$CO_2^-$, at least one of $R^1$, $R^2$, $R^3$ and R does not represent a hydrogen atom.

The monovalent organic group having 1 to 20 carbon atoms which may be represented by $R^1$, $R^2$, $R^3$, R and $R^a$ is exemplified by: a monovalent hydrocarbon group having 1 to 20 carbon atoms; a group obtained by combining the hydrocarbon group with at least one group selected from the set consisting of —O—, —CO—, —CO—O—, —O—CO—, —O—CO—O—, —$NR^X$—, —$SO_2$—O— and —S—, or a group obtained by replacing a part of carbon atoms constituting the hydrocarbon group with a hetero atom, and the like, wherein, a part or all of hydrogen atoms included in the monovalent hydrocarbon group are unsubstituted or substituted with a substituent. Examples of the substituent include, a hydroxy group, a mercapto group, a cyano group, a halogen atom, =O that substitutes for two hydrogen atoms bound to an identical carbon atom, and the like.

$R^X$ represents a hydrogen atom or a monovalent organic group having 1 to 20 carbon atoms.

Examples of the monovalent hydrocarbon group having 1 to 20 carbon atoms include a monovalent alkyl group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent alkyl group having 1 to 20 carbon atoms include: linear alkyl groups such as a methyl group, an ethyl group, a n-propyl group and a n-butyl group; branched alkyl groups such as an i-propyl group, an i-butyl group, a sec-butyl group and a t-butyl group.

Examples of the monovalent alicyclic hydrocarbon group having 3 to 20 carbon atoms include: groups having an alicyclic ring derived from norbornane, tricyclodecane, tetracyclododecane or adamantane, or a cycloalkane such as cyclopropane, cyclobutane, cyclopentane, cyclohexane, cycloheptane or cyclooctane; groups obtained by introducing to these groups having an alicyclic ring, a substituent such as one or more types of or one or more of a linear, branched or cyclic alkyl group having 1 to 4 carbon atoms such as a methyl group, an ethyl group, a n-propyl group, an i-propyl group, a n-butyl group, a 1-methylethyl group, a 1-methylpropyl group, a 2-methylpropyl group and a t-butyl group, and the like.

Examples of the monovalent aromatic hydrocarbon group having 6 to 20 carbon atoms include a phenyl group, a tolyl group, a xylyl group, a mesityl group, a cumenyl group, a benzyl group, a phenethyl group, a naphthyl group, and the like.

Examples of the ring structure which may be taken together represented by two of $R^1$, $R^2$, $R^3$ and R by binding with each other include ring structures included in compounds represented by the formulae (1-1-2) to (1-1-5), (1-2-2) and (1-2-4) described later, and the like.

Examples of the monovalent organic group which may be represented by $R^X$ include groups similar to those exemplified in connection with $R^1$, $R^2$, $R^3$ and R above, and the like.

Examples of the halogen atom include a fluorine atom, a chlorine atom, a bromine atom, an iodine atom, and the like. Of these, a fluorine atom is preferred.

Examples of the monovalent onium cation which may be represented by $M^+$ include sulfonium cations represented by the following formula (M'), iodonium cations represented by the following formula (M"), and the like.

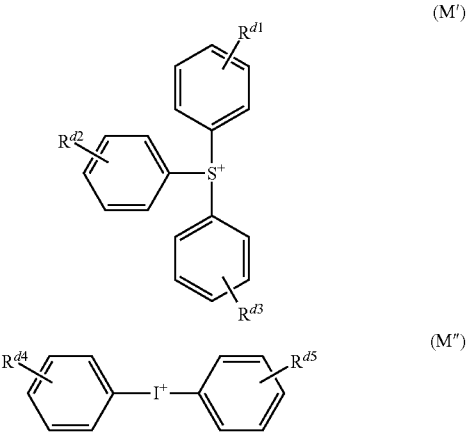

In the above formula (M'), $R^{d1}$ to $R^{d3}$ each independently represent a hydrogen atom, an alkyl group, an alkoxy group, a hydroxy group or a halogen atom. In the above formula (M"), $R^{d4}$ and $R^{d5}$ each independently represent a hydrogen atom, an alkyl group, an alkoxy group, a hydroxy group or a halogen atom.

Examples of the monovalent sulfonium cation which may be represented by $M^+$ include a triphenylsulfonium cation, a 4-hydroxyphenyldiphenylsulfonium cation, a 4-cyclohexylphenyldiphenylsulfonium cation, a 4-methanesulfonylphenyldiphenylsulfonium cation, a (4-t-butoxyphenyl)diphenylsulfonium cation, a bis(4-t-butoxyphenyl)phenylsulfonium cation, a 4-cyclohexylsulfonylphenyldiphenylsulfonium cation, and the like.

Examples of the monovalent iodonium cation which may be represented by $M^+$ include a diphenyliodonium cation, a bis(4-t-butylphenyl) iodonium cation, a 4-t-butoxyphenylphenyliodonium cation, a 4-methoxyphenylphenyliodonium cation, and the like.

Of these, a sulfonium cation is preferred, and a triphenylsulfonium cation is more preferred.

The compound (I) represented by the above formula (1) is preferably any one of compounds represented by the above formulae (1-1-1) to (1-1-5), or a mixture of these compounds.

In the above formulae (1-1-1) to (1-1-5), $M^+$, $A^-$, $R^1$, $R^2$, $R^3$ and R are as defined in the above formula (1); and $R^{p1}$, $R^{p2}$, $R^{p3}$ and $R^{p4}$ each independently represent a divalent organic group.

When the compound (I) represented by the above formula (1) is represented by one of the above specific formulae, the diffusion of the acid diffusion control agent, etc., in the resist film formed can be further inhibited according to the photoresist composition, leading to an improvement of a contrast between a light-exposed site and a light-unexposed site to enable a resist pattern more superior in characteristics such as an LWR performance to be formed.

Specific examples of the compound (I) represented by the above formulae (1-1-1) to (1-1-5) include:

compounds represented by the above formula (1-1-1) such as compounds represented by the following formulae (a-1) to (a-12), (a-24), (a-25) and (a-28) to (a-33), and the like;

compounds represented by the above formula (1-1-2) such as compounds represented by the following formulae (a-13) to (a-16), (a-26) and (a-27), and the like;

compounds represented by the above formula (1-1-3) such as compounds represented by the following formulae (a-17) to (a-20), and the like.

Examples of the compound represented by the above formula (1-1-4) include compounds represented by the following formulae (a-21) and (a-22), and the like.

Examples of the compound represented by the above formula (1-1-5) include compounds represented by the following formula (a-23), and the like.

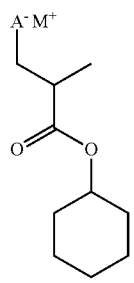

(a-1)

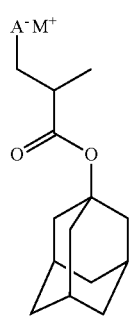

(a-2)

-continued

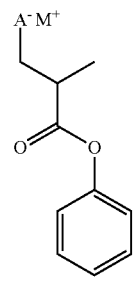

(a-3)

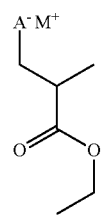

(a-4)

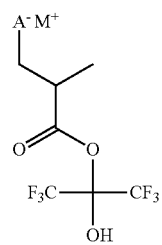

(a-5)

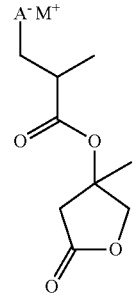

(a-6)

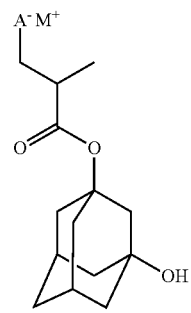

(a-7)

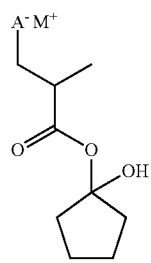

(a-8)

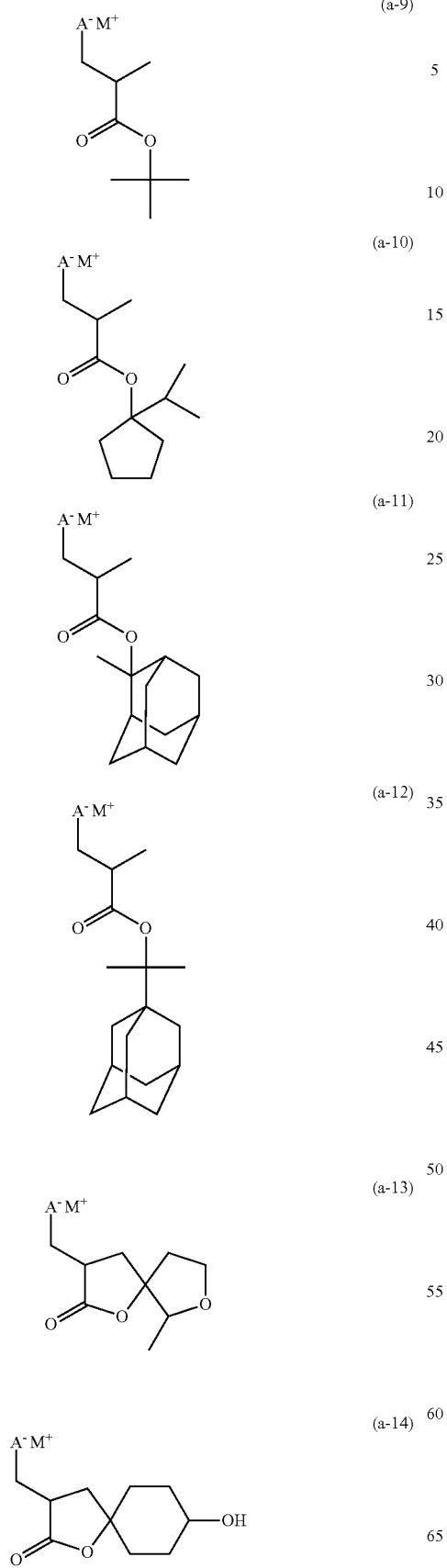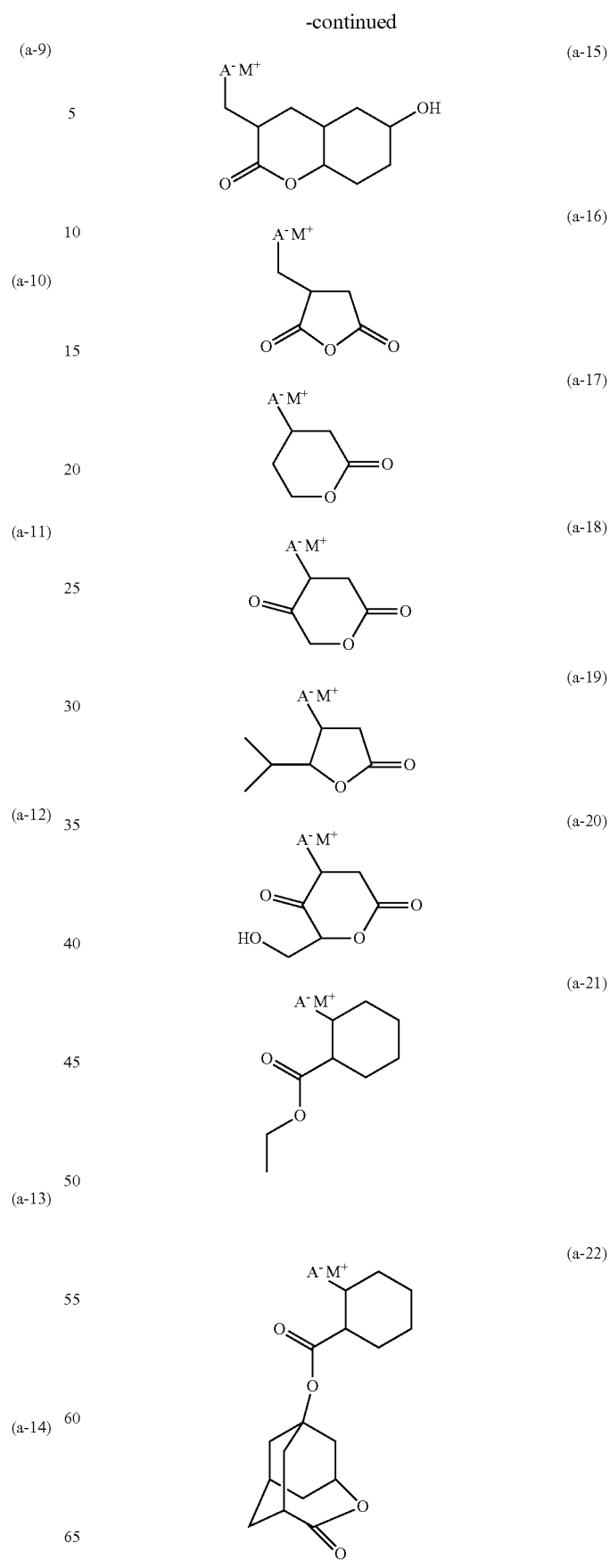

-continued
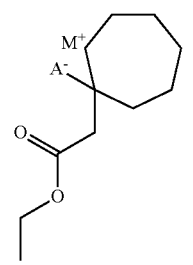
(a-23)
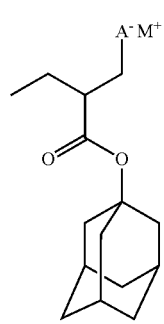
(a-24)
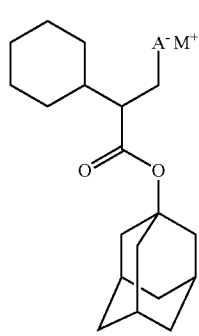
(a-25)
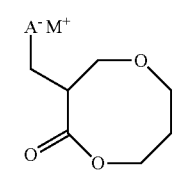
(a-26)
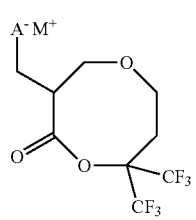
(a-27)
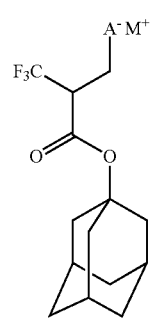
(a-28)
-continued
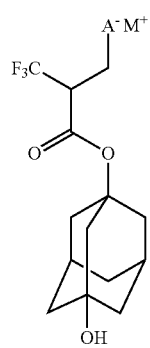
(a-29)
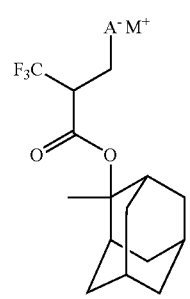
(a-30)
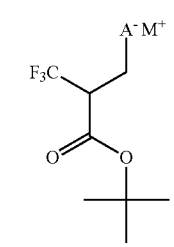
(a-31)
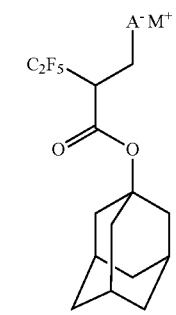
(a-32)
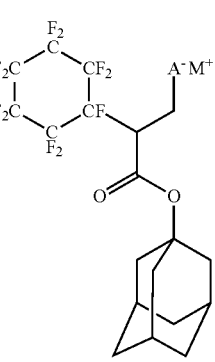
(a-33)
In the above formula, $A^-$ and $M^+$ are as defined in the above formula (1).

Of the compounds represented by the above formulae (1-1-1) to (1-1-5), the compound represented by the formula (1-1-1) is preferred.

In addition, it is also preferred that the compound (I) represented by the above formula (1) is any one of compounds represented by the above formulae (1-2-1) to (1-2-4), or a mixture of these compounds.

In the above formulae (1-2-1) to (1-2-4), $M^+$, $A^-$, $R^1$, $R^2$, $R^3$, R and R are as defined in the above formula (1); and $R^{p1}$ and $R^{p2}$ each independently represent a divalent organic group.

When the compound (I) represented by the above formula (1) is represented by one of the above specific formulae, the diffusion of the acid diffusion control agent, etc., in the resist film formed can be further inhibited according to the photoresist composition, leading to an improvement of a contrast between a light-exposed site and a light-unexposed site to enable a resist pattern more superior in characteristics such as an LWR performance to be formed.

Specific examples of the compounds (I) represented by the above formulae (1-2-1) to (1-2-4) include
the compounds represented by the above formula (1-2-1) such as compounds represented by the following formulae (b-1) to (b-4) and the like;
the compounds represented by the above formula (1-2-2) such as compounds represented by the following formulae (b-5) to (b-8) and the like;
the compounds represented by the above formula (1-2-3) such as compounds represented by the following formula (b-9) and the like; compounds represented by the above formula (1-2-4) such as compounds represented by the following formulae (b-10) to (b-17) and the like.

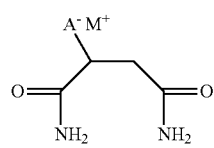

(b-1)

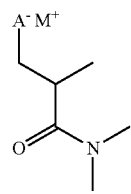

(b-2)

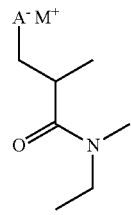

(b-3)

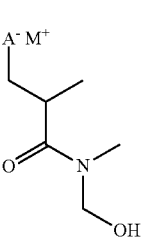

(b-4)

-continued

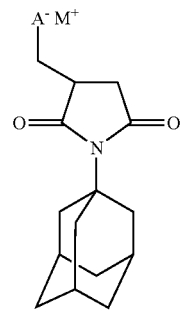

(b-5)

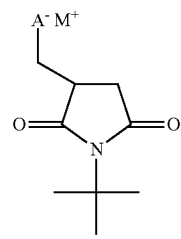

(b-6)

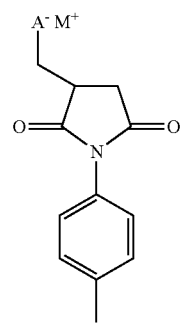

(b-7)

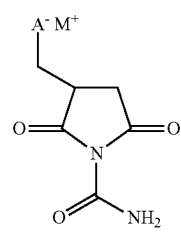

(b-8)

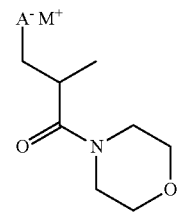

(b-9)

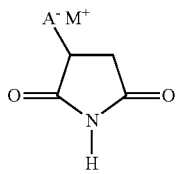

(b-10)

(b-11)
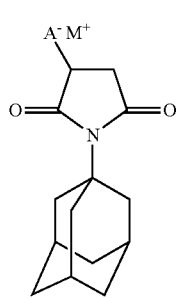

(b-12)
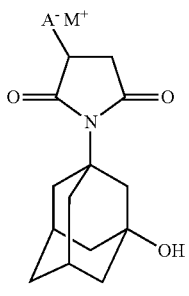

(b-13)
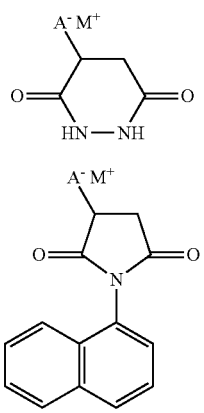

(b-14)
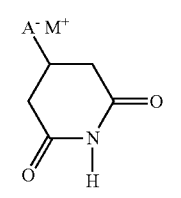

(b-15)

(b-16)

(b-17)
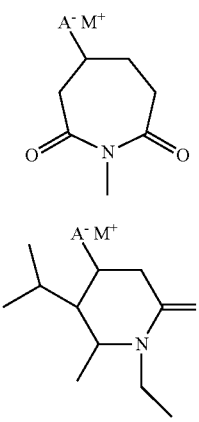

In the above formulae, $A^-$ and $M^+$ are as defined in the above formula (1).

Among the compounds represented by the above formulae (1-2-1) to (1-2-4), compounds represented by the formula (1-2-4) are preferred.

In addition, it is also preferred that the compound (I) represented by the above formula (1) is represented by the above formula (2).

In the above formula (2), $A^-$, $M^+$ and $R^a$ are as defined in the above formula (1); and n is an integer of 0 to 5.

When the compound (I) represented by the above formula (1) is represented by the above formula (2), the diffusion of the acid diffusion control agent, etc., in the resist film formed can be further inhibited according to the photoresist composition, leading to an improvement of a contrast between a light-exposed site and a light-unexposed site to enable a resist pattern more superior in characteristics such as an LWR performance to be formed.

Specific examples of the compound (I) represented by the above formula (2) include the compounds represented by the above formulae (b-10) to (b-12) and (b-14) to (b-16) and the like.

Production Method of Compound (I)

Although the production method of the compound (I) is not particularly limited, a method similar to the method described in detail in Production Method of Compound described later is preferred. It is to be noted that as a material compound used in the production of the compound (I), a corresponding compound may be appropriately selected.

Optional Components

Examples of the optional component which may be contained in the photoresist composition include the acid diffusion control agent (B) and the acid generating agent (C) and the like as in the photoresist composition (I) described later, as well as the acid generating agent (D) and the acid diffusion control agent (E) and the like as in the photoresist composition (II) described later.

The photoresist compositions (I) and (II) as preferred embodiments of the photoresist composition will be described in detail below. Note that the photoresist composition (I) is suitable for an exposure by way of a radioactive ray such as an ArF excimer laser beam (wavelength: 193 nm), whereas the photoresist composition (II) is suitable for an exposure by way of a radioactive ray such as an electron beam or EUV light (wavelength: 13.5 nm).

Photoresist Composition (I)

The photoresist composition (I) according to an embodiment of the present invention contains the polymer (A), and the acid diffusion control agent (B), and the acid diffusion control agent (B) contains the compound (I). In addition, the photoresist composition (I) may contain the acid generating agent (C) as a favorable component. Also, the photoresist composition (I) may contain other optional component(s) such as a fluorine atom-containing polymer (hereinafter, may be also referred to as "polymer (F)"), (G) a solvent, and (H) an uneven distribution accelerator within a range not leading to impairment of the effects of the embodiment of the present invention. Hereinafter, each component will be explained in detail.

(A) Polymer

The polymer (A) serves as a base polymer. The term "base polymer" as referred to means a polymer to be a principal component of a polymer that constitutes the resist film formed from the photoresist composition, and preferably a polymer accounting for no less than 50% by mass with respect to the total mass of the polymers constituting the resist film. The polymer (A) has the structural unit (I). Moreover, it is preferred that in the photoresist composition (I), the acid-labile group in the structural unit (I) is polar, or the polymer (A) has the structural unit (II). Accordingly, a uniform resist film can be formed. Furthermore, the polymer (A) may have other structural unit within a range not leading to impairment of the effects of the present invention. Note that the polymer (A) may include two or more types of each structural unit. Hereinafter, each structural unit will be explained in detail.

Structural Unit (I)

The structural unit (I) includes an acid-labile group. Due to including the acid-labile group in the structural unit (I), the acid-labile group at a light-exposed site is dissociated upon irradiation with a radioactive ray. As a result, the polymer (A) at the light-exposed site becomes hydrophilic, leading to generation of the difference in the rate of dissolution in a developer solution between the light-exposed site and the light-unexposed site, whereby a desired resist pattern can be formed. It is to be noted that the "acid-labile group" as referred to means, for example, a group that substitutes for a hydrogen atom included in a polar functional group such as a hydroxy group or a carboxy group, and is dissociated in the presence of an acid.

Examples of the structural unit (I) include structural units represented by the following formulae (7-1) and (7-2), and the like.

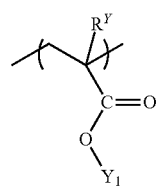

(7-1)

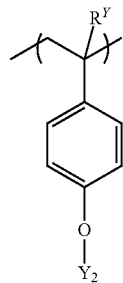

(7-2)

In the above formulae (7-1) and (7-2), $R^Y$ represents a hydrogen atom, a fluorine atom, a methyl group or a trifluoromethyl group; and $Y_1$ and $Y_2$ represent an acid-labile group.

The acid-labile group represented by $Y_1$ is preferably a group represented by the following formula (Y-1).

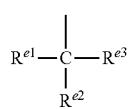

(Y-1)

In the above formula (Y-1), $R^{e1}$, $R^{e2}$ and $R^{e3}$ each independently represent an alkyl group having 1 to 4 carbon atoms or a monovalent alicyclic hydrocarbon group having 3 to 20 carbon atoms; $R^{e2}$ and $R^{e3}$ may taken together represent a divalent alicyclic hydrocarbon group having 3 to 20 carbon atoms by binding with each other together with the carbon atom to which $R^{e2}$ and $R^{e3}$ bond.

Examples of the alkyl group having 1 to 4 carbon atoms which may be represented by $R^{e1}$, $R^{e2}$ and $R^{e3}$ include a methyl group, an ethyl group, a n-propyl group, an i-propyl group, a n-butyl group, a 2-methylpropyl group, a 1-methylpropyl group, a t-butyl group, and the like.

Examples of the monovalent aliphatic cyclic hydrocarbon group having 3 to 20 carbon atoms which may be represented by $R^{e1}$, $R^{e2}$ and $R^{e3}$, and the divalent alicyclic hydrocarbon group having 3 to 20 carbon atoms taken together represented by $R^{e2}$ and $R^{e3}$ by binding with each other together with the carbon atom to which $R^{e2}$ and $R^{e3}$ bond include groups having an alicyclic hydrocarbon skeleton such as: groups having a bridged skeleton such as an adamantane skeleton or a norbornane skeleton or a monocyclic cycloalkane skeleton such as cyclopentane or cyclohexane; and groups obtained by introducing to these groups, a substituent such as one or more types of or one or more of a linear, branched or cyclic alkyl group having 1 to 10 carbon atoms such as e.g., a methyl group, an ethyl group, a n-propyl group and an i-propyl group.

Of these, in light of a possible improvement of the shape of the resist pattern after the development, groups having a monocyclic cycloalkane skeleton are preferred.

The acid-labile group represented by $Y_2$ is preferably a group represented by the following formula (Y-2).

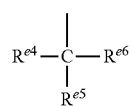

(Y-2)

In the above formula (Y-2), $R^{e4}$, $R^{e5}$ and $R^{e6}$ each independently represent a hydrogen atom, an alkyl group having 1 to 20 carbon atoms, a monovalent alicyclic hydrocarbon group having 3 to 20 carbon atoms, an alkoxy group having 1 to 20 carbon atoms or an oxyalicyclic hydrocarbon group having 1 to 20 carbon atoms, wherein at least one of $R^{e4}$, $R^{e5}$ and $R^{e6}$ does not represent a hydrogen atom.

Examples of the an alkyl group having 1 to 20 carbon atoms include linear alkyl groups such as a methyl group, an ethyl group, a n-propyl group and a n-butyl group; branched alkyl groups such as an i-propyl group, an i-butyl group, a sec-butyl group and a t-butyl group; and the like.

Examples of the monovalent alicyclic hydrocarbon group having 3 to 20 carbon atoms include groups having an alicyclic ring derived from norbornane, tricyclodecane, tetracyclododecane or adamantane, or a cycloalkane such as cyclopropane, cyclobutane, cyclopentane, cyclohexane, cycloheptane or cyclooctane; groups obtained by introducing to these groups having an alicyclic ring, a substituent such as e.g., one or more types of or one or more of linear, branched or cyclic alkyl groups having 1 to 4 carbon atoms such as a methyl group, an ethyl group, a n-propyl group, an i-propyl group, a n-butyl group, a 1-methylethyl group, a 1-methylpropyl group, a 2-methylpropyl group and a t-butyl group; and the like.

Examples of the alkoxy group having 1 to 20 carbon atoms include a methoxy group, an ethoxy group, a n-propoxy group, an i-propoxy group, and the like.

Examples of the oxyalicyclic hydrocarbon group having 1 to 20 carbon atoms include a cyclobutyloxy group, a cyclohexyloxy group, a cyclohexylmethyloxy group, a cyclohexylethyloxy group, and the like. Of these, a cyclohexylmethyloxy group or a cyclohexylethyloxy group is preferred.

Examples of the structural unit (I) include:

the structural unit (I) represented by the above formula (7-1) such as structural units represented by the formulae (7-1-1) to (7-1-7) and the like;

the structural unit (I) represented by the above formula (7-2) such as structural units represented by the formulae (7-2-1) to (7-2-3) and the like;

Examples of the structural unit (I) other than the structural units represented by the above formulae (7-1) and (7-2) include structural units represented by the formula (7-3-1), and the like.

(7-1-1)

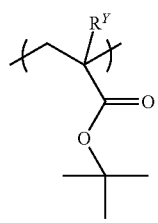

(7-1-2)

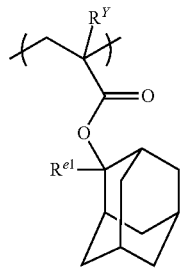

(7-1-3)

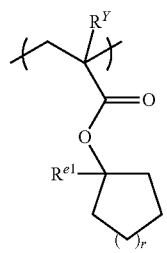

(7-1-4)

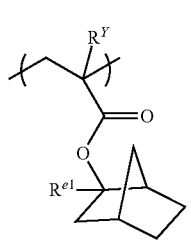

-continued (7-1-5)

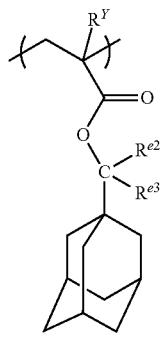

(7-1-6)

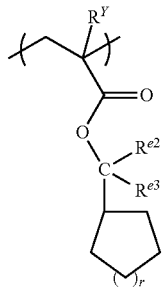

(7-1-7)

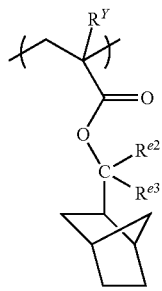

(7-2-1)

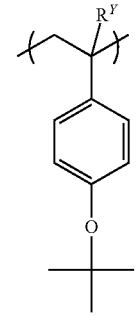

(7-2-2)

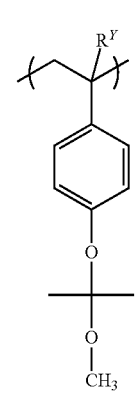

(7-2-3)

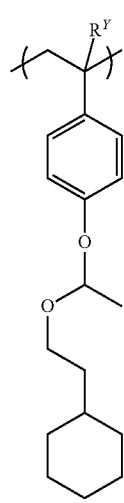

(7-3-1)

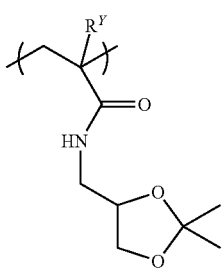

Examples of the monovalent hydrocarbon group having 1 to 20 carbon atoms include groups similar to those exemplified in connection with the monovalent hydrocarbon group having 1 to 20 carbon atoms in the monovalent organic group having 1 to 20 carbon atoms which may be represented by $R^1$, $R^2$, $R^3$, R and $R^a$, and the like.

Examples of the polar group include a hydroxy group, a carboxy group, an oxo group, a cyano group, a sulfo group, a mercapto group, an amino group, and the like. Of these, a hydroxy group and a cyano group are preferred.

Examples of the structural unit (II) include structural units represented by the following formulae, and the like.

(3-1)

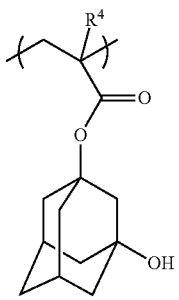

(3-2)

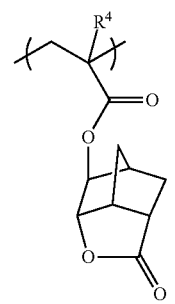

(3-3)

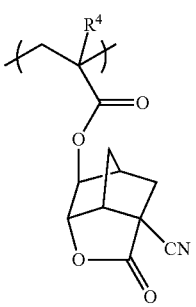

(3-4)

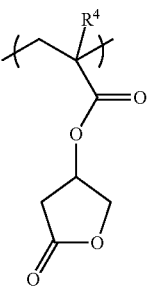

In the above formulae (7-1-1) to (7-3-1), $R^Y$ is as defined in the formula (7-1) and (7-2); $R^{e1}$, $R^{e2}$ and $R^{e3}$ are as defined in the formula (Y-1); and r is each independently an integer of 1 to 3.

The proportion of the structural unit (I) contained with respect to all the structural units constituting the polymer (A) is preferably 5 mol % to 90 mol %, more preferably 10 mol % to 80 mol %, and still more preferably 20 mol % to 70 mol %. When the proportion of the structural unit (I) contained falls within the above range, the shape of the resist pattern after the development can be effectively improved.

Structural Unit (II)

The structural unit (II) is represented by the above formula (3). When the photoresist composition (I) further includes the structural unit (II), a uniform resist film can be formed.

In the above formula (3), $R^4$ represents a hydrogen atom, a fluorine atom, a methyl group or a trifluoromethyl group; L represents a single bond, —CO—O— or —CO—NH—; and $R^5$ represents an acid-nonlabile and polar group. It is to be noted that the "acid-nonlabile group" as referred to means a group that is not dissociated due to an action of the acid generated from the acid generating agent upon an exposure, or a group that is comparatively hardly dissociated due to an action of the acid.

Examples of the acid-nonlabile and polar group represented by $R^5$ include:

(1) monovalent hydrocarbon groups having 1 to 20 carbon atoms and having a polar group;

(2) monovalent hydrocarbon groups having 1 to 20 carbon atoms and having —O— and/or —CO—O— in their structure;

(3) monovalent hydrocarbon groups having 1 to 20 carbon atoms and having a polar group, and —O— and/or —CO—O— in their structure; and the like.

(3-5) 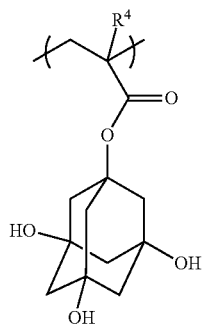
(3-6) 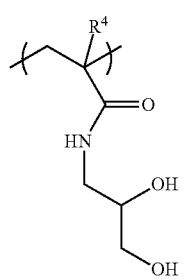
(3-7) 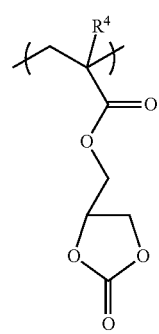
(3-8) 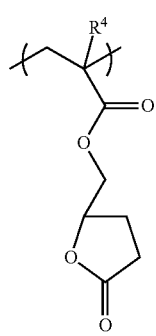
(3-9) 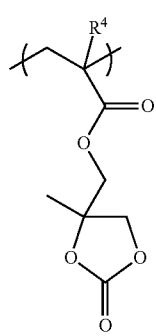
(3-10) 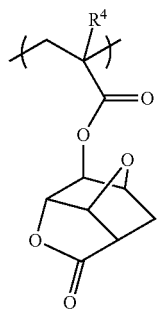
(3-11) 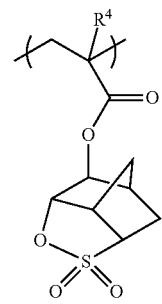
(3-12) 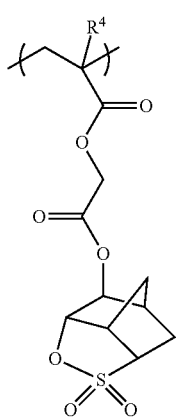
(3-13) 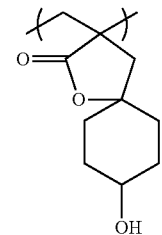
(3-14) 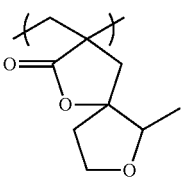
In the above formulae, $R^4$ is as defined in the above formula (3).
Of these, the structural units represented by the above formulae (3-1), (3-2) and (3-3) are preferred, and the structural units represented by the above formula (3-2) are more preferred.

The proportion of the structural unit (II) contained with respect to all the structural units constituting the polymer (A) is preferably 5 mol % to 95 mol %, more preferably 10 mol % to 90 mol %, and still more preferably 20 mol % to 70 mol %.

Other Structural Unit

The polymer (A) may have other structural unit except for the structural units (I) and (II). Examples of the other structural unit include structural units derived from N,N-dimethyl methacrylamide, p-hydroxystyrene or the like, and the like.

Synthesis Method of Polymer (A)

The polymer (A) can be synthesized in accordance with a common method of radical polymerization or the like. For example, the polymer (A) is preferably synthesized by: (1) a method including adding a solution containing a monomer and a radical initiator dropwise to a solution containing a reaction solvent or a monomer to permit a polymerization reaction; (2) a method including separately adding a solution containing a monomer and a solution containing a radical initiator dropwise to a solution containing a reaction solvent or a monomer to permit a polymerization reaction; (3) a method including separately adding a plurality of kinds of solutions containing each monomer, and a solution containing a radical initiator to a solution containing a reaction solvent or a monomer to permit a polymerization reaction; (4) a method including permitting a polymerization reaction of a solution containing a monomer and a radical initiator in the absence of a solvent or in a reaction solvent; or the like.

It is to be noted that when the reaction is permitted through adding the monomer solution to the monomer solution dropwise, the amount of the monomer in the monomer solution added dropwise with respect to the total amount of the monomer used in the polymerization is preferably no less than 30 mol %, more preferably no less than 50 mol %, and still more preferably no less than 70 mol %.

The reaction temperature in these methods may be appropriately predetermined in accordance with the initiator species. The reaction temperature is typically 30° C. to 150° C., preferably 40° C. to 150° C., and more preferably 50° C. to 140° C. The time period of the dropwise addition may vary depending on conditions such as the reaction temperature, the initiator type and the monomer to be reacted and the like, and is typically 30 min to 8 hours, preferably 45 min to 6 hours, and more preferably 1 hour to 5 hours. In addition, although a total reaction time period including the time period of dropwise addition may also vary depending on conditions similarly to the time period of the dropwise addition, the total reaction time period is typically 30 min to 12 hours, preferably 45 min to 12 hours, and more preferably 1 to 10 hours.

Examples of the radical initiator for use in the polymerization include: azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), dimethyl 2,2'-azobis(2-methylpropionate) and dimethyl 2,2'-azobisisobutyrate; peroxide radical initiators such as benzoylperoxide, t-butylhydroperoxide and cumenehydroperoxide; and the like. Of these, AIBN and dimethyl 2,2'-azobis(2-methylpropionate) are preferred. It is to be noted that the radical initiator may be used either alone or in combination of two or more thereof.

The reaction solvent is other than solvents that inhibit polymerization (nitrobenzene having a polymerization inhibitory effect, a mercapto compound having a chain transfer effect, etc.), and may be used as long as it can dissolve the monomer. Examples of the reaction solvent include, alcohols, ethers, ketones, amides, esters, lactones, nitriles, mixed solvents of these, and the like. These solvents may be used either alone or in combination of two or more types thereof.

The polymer obtained by the polymerization reaction is preferably recovered by a reprecipitation technique. More specifically, after completion of the polymerization reaction, the intended polymer is recovered in the form of powder through charging the polymerization mixture into a reprecipitation solvent. As the reprecipitation solvent, alcohols, alkanes and the like may be used either alone or in combination of two or more types thereof. Moreover, in addition to the reprecipitation technique, a liquid separating operation, a column operation, an ultrafiltration operation or the like enables the polymer to be recovered through eliminating low molecular components such as monomers and oligomers.

The polystyrene equivalent weight average molecular weight (Mw) of the polymer (A) as determined by gel permeation chromatography (GPC) is preferably 1,000 to 50,000, more preferably 2,000 to 40,000, and still more preferably 3,000 to 30,000. When the Mw of the polymer (A) is less than 1,000, heat resistance as a resist may be deteriorated. On the other hand, when the Mw of the polymer (A) is greater than 50,000, developability as a resist may be impaired.

(B) Acid Diffusion Control Agent

The acid diffusion control agent (B) contains the compound (I). In addition, the acid diffusion control agent (B) may contain an acid diffusion control agent other than the compound (I) within a range not leading to impairment of the effects of the present invention. The acid diffusion control agent (B) is a component that controls the diffusion of an acid generated upon an exposure. Due to containing the acid diffusion control agent (B), the photoresist composition (I) enables the diffusion of the acid diffusion control agent (B) per se in the resist film to be inhibited, and consequently a contrast between a light-exposed site and a light-unexposed site can be enhanced.

Examples of the acid diffusion control agent other than the compound (I) include acid diffusion control agents similar to those exemplified for the acid diffusion control agent (E) in connection with the photoresist composition (II) described later, and the like.

The percentage content of the compound (I) in the acid diffusion control agent (B) is preferably no less than 30% by mass, more preferably no less than 50% by mass, and still more preferably no less than 70% by mass. When the percentage content of the compound (I) falls within the above range, the diffusion of the acid can be more appropriately inhibited.

The content of the acid diffusion control agent (B) with respect to 100 parts by mass of the total amount of the polymers contained in the photoresist composition (I) is preferably 1 part by mass to 100 parts by mass, more preferably 5 parts by mass to 80 parts by mass, and still more preferably 10 parts by mass to 50 parts by mass. When the content is less than 1 part by mass, the effect of the acid diffusion control agent (B) may be deteriorated. On the other hand, when the content is greater than 100 parts by mass, sensitivity of the resist film formed may be significantly decreased.

(C) Acid Generating Agent

The acid generating agent (C) is a compound that differs from the compound (I). The acid generating agent (C) is a radiation-sensitive component that generates an acid upon an exposure. When the photoresist composition (I) contains the acid generating agent (C), the sensitivity can be enhanced, and consequently the contrast of the resist pattern formed can be improved. It is to be noted that the acid generating agent (C) may be used either alone or in combination of two or more types thereof.

Examples of the acid generating agent (C) include onium salt compounds such as an iodonium salt, a sulfonium salt and a tetrahydrothiophenium salt, sulfonic acid compounds, and the like.

Examples of the iodonium salt include diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, cyclohexyl-2-oxocyclohexylmethylsulfonium trifluoromethanesulfonate, dicyclohexyl-2-oxocyclohexylsulfonium trifluoromethanesulfonate, 2-oxocyclohexyldimethylsulfonium trifluoromethanesulfonate, 4-hydroxy-1-naphthyldimethylsulfonium trifluoromethanesulfonate, triphenylsulfonium 2-(adamantan-1-yl)-1,1-difluoroethane-1-sulfonate, and the like.

Examples of the tetrahydrothiophenium salt include 4-hydroxy-1-naphthyltetrahydrothiophenium trifluoromethanesulfonate, 4-hydroxy-1-naphthyltetrahydrothiophenium nonafluoro-n-butanesulfonate, 4-hydroxy-1-naphthyltetrahydrothiophenium perfluoro-n-octanesulfonate, 1-(1-naphthylacetomethyl)tetrahydrothiophenium trifluoromethanesulfonate, 1-(1-naphthylacetomethyl)tetrahydrothiophenium nonafluoro-n-butanesulfonate, 1-(1-naphthylacetomethyl)tetrahydrothiophenium perfluoro-n-octanesulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, and the like.

Examples of the sulfonic acid compound include trifluoromethanesulfonyl bicyclo[2.2.1]hept-5-ene-2,3-dicarbodiimide, nonafluoro-n-butanesulfonyl bicyclo[2.2.1]hept-5-ene-2,3-dicarbodiimide, perfluoro-n-octanesulfonyl bicyclo[2.2.1]hept-5-ene-2,3-dicarbodiimide, N-hydroxysuccinimide trifluoromethanesulfonate, N-hydroxysuccinimide nonafluoro-n-butanesulfonate, N-hydroxysuccinimide perfluoro-n-octanesulfonate, 1,8-naphthalenedicarboxylic imide trifluoromethanesulfonate, and the like.

Of these, onium salt compounds are preferred, sulfonium salts are more preferred, and triphenylsulfonium 2-(adamantan-1-yl)-1,1-difluoroethane-1-sulfonate is still more preferred.

The content of the acid generating agent (C) with respect to 100 parts by mass of the polymers contained in the photoresist composition (I) is, in light of a securement of sensitivity and developability as a resist, preferably 0.1 parts by mass to 50 parts by mass, more preferably 0.2 parts by mass to 40 parts by mass, and still more preferably 0.5 parts by mass to 30 parts by mass. When the content of the acid generating agent (C) is less than 0.1 parts by mass, the sensitivity and the developability tend to be deteriorated. On the other hand, when the content is greater than 50 parts by mass, transparency to radioactive rays is decreased, and thus a rectangular resist pattern tends to be hardly obtained.

(F) Polymer

The polymer (F) is a fluorine atom-containing polymer. The polymer (F) preferably has a high percentage content of fluorine atoms than that of the polymer (A). Accordingly, the polymer (F) can be unevenly distributed effectively on the surface layer of the resist film. Consequently, hydrophobicity of the surface layer of the resist film can be improved, and even in a case where liquid immersion lithography is carried out, favorable inhibition of elution of substances, as well as a sufficiently great receding contact angle between the resist film and the liquid immersion liquid can be attained, allowing an effect such as avoiding water droplets from remaining upon a scanning exposure at high speed, etc., to be achieved; therefore, usability of the photoresist composition for liquid immersion lithography is enhanced.

The structure of the polymer (F) is not particularly limited, which may be involve: (1) a fluorine-containing polymer that is insoluble in a developer solution per se, and becomes alkali-soluble by an action of an acid; (2) a fluorine-containing polymer that is soluble in a developer solution per se, and has an alkali-solubility that increases by an action of an acid; (3) a fluorine-containing polymer that is insoluble in a developer solution per se, and becomes alkali-soluble by an action of an alkali; (4) a fluorine-containing polymer that is soluble in a developer solution per se, and has an alkali-solubility that increases by an action of an alkali; or the like.

Exemplary modes of the polymer (F) may involve:

a structure in which a fluorinated alkyl group bonds to its main chain;

a structure in which a fluorinated alkyl group bonds to its side chain;

a structure in which a fluorinated alkyl group bonds to its main chain and a side chain; and the like.

Examples of the monomer that gives the structure in which a fluorinated alkyl group bonds to its main chain include α-trifluoromethylacrylate compounds, β-trifluoromethylacrylate compounds, α,β-trifluoromethylacrylate compounds, compounds derived by substituting a hydrogen atom of one or more types of vinyl moieties by a fluorinated alkyl group such as a trifluoromethyl group, and the like.

Examples of the monomer that gives the structure in which a fluorinated alkyl group bonds to its side chain include alicyclic olefin compounds such as norbornene having a fluorinated alkyl group and/or a derivative thereof as a side chain, ester compounds of acrylic acid or methacrylic acid having a fluorinated alkyl group and/or a derivative thereof as a side chain, olefins having a fluorinated alkyl group and/or a derivative thereof as one or more types of side chain (a site excluding a double bond), and the like.

Examples of the monomer that gives the structure in which a fluorinated alkyl group bonds to its main chain and side chain include ester compounds of α-trifluoromethylacrylic acid, β-trifluoromethylacrylic acid, α,β-trifluoromethylacrylic acid or the like with a fluorinated alkyl group and/or a derivative thereof as a side chain, compounds derived by substituting hydrogen of one or more types of vinyl moieties by a fluorinated alkyl group and introducing to a side chain of the compound, a fluorinated alkyl group such as a trifluoromethyl group and/or a derivative thereof; alicyclic olefin compounds derived by substituting hydrogen bonded to one or more types of double bonds by a fluorinated alkyl group such as a trifluoromethyl group, etc., and having a fluorinated alkyl group and/or a derivative thereof as a side chain; and the like. The alicyclic olefin compound as referred to herein means a compound that includes a double bond in a part of its ring.

The polymer (F) preferably has the structural unit (f1) represented by the following formula (8) and/or the structural unit (f2) represented by the following formula (9). Also, the polymer (F) may have "other structural unit" except for the structural unit (f1) and the structural unit (f2). The polymer (F) may have two or more types of each structural unit. Each structural unit will be described in detail below.

Structural Unit (f1)

The structural unit (f1) is represented by the following formula (8).

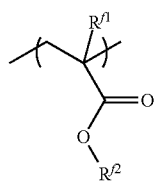

(8)

In the above formula (8), $R^{f1}$ represents a hydrogen atom, a fluorine atom, a methyl group or a trifluoromethyl group; $R^2$ represents a linear or branched alkyl group having 1 to 6 carbon atoms and having a fluorine atom or a monovalent alicyclic hydrocarbon group having 4 to 20 carbon atoms and having a fluorine atom, wherein a part or all of hydrogen atoms included in the alkyl group and the alicyclic hydrocarbon group are unsubstituted or substituted.

Examples of the linear or branched alkyl group having 1 to 6 carbon atoms include a methyl group, an ethyl group, a propyl group, a butyl group, and the like.

Examples of the monovalent alicyclic hydrocarbon group having 4 to 20 carbon atoms include a cyclopentyl group, a cyclopentylpropyl group, a cyclohexyl group, a cyclohexylmethyl group, a cycloheptyl group, a cyclooctyl group, a cyclooctylmethyl group, and the like.

Examples of the monomer that gives the structural unit (f1) include trifluoromethyl (meth)acrylate, 2,2,2-trifluoroethyl (meth)acrylate, perfluoroethyl (meth)acrylate, perfluoro-n-propyl (meth)acrylate, perfluoro-i-propyl (meth) acrylate, perfluoro-n-butyl (meth)acrylate, perfluoro-i-butyl (meth)acrylate, perfluoro-t-butyl (meth)acrylate, perfluorocyclohexyl (meth)acrylate, 2-(1,1,1,3,3,3-hexafluoro)propyl (meth)acrylate, 1-(2,2,3,3,4,4,5,5-octafluoro)pentyl (meth) acrylate, 1-(2,2,3,3,4,4,5,5-octafluoro)hexyl (meth)acrylate, perfluorocyclohexylmethyl (meth)acrylate, 1-(2,2,3,3,3-pentafluoro)propyl (meth)acrylate, 1-(2,2,3,3,4,4,4-heptafluoro)penta (meth)acrylate, 1-(3,3,4,4,5,5,6,6,7,7,8,8,9,9,10,10,10-heptadecafluoro)decyl (meth)acrylate, 1-(5-trifluoromethyl-3,3,4,4,5,6,6,6-octafluoro)hexyl (meth) acrylate, and the like.

Examples of the structural unit (f1) preferred include structural units represented by the following formulae (8-1) and (8-2).

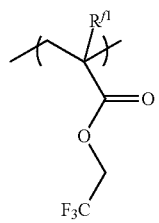

(8-1)

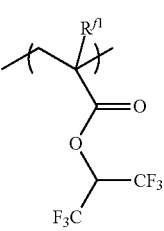

(8-2)

In the above formulae (8-1) and (8-2), $R^{f1}$ is as defined in the above formula (8). Of these, the structural unit represented by the formula (8-1) is more preferred.

The proportion of the structural unit (f1) contained with respect to all the structural units constituting the polymer (F) is preferably 10 mol % to 70 mol %, and more preferably 20 mol % to 50 mol %.

Structural Unit (f2)

The structural unit (f2) is represented by the following formula (9).

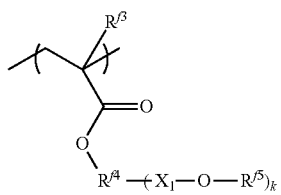

(9)

In the above formula (9), $R^{f3}$ represents a hydrogen atom, a fluorine atom, a methyl group or a trifluoromethyl group; $R^{f4}$ represents a linking group having a valency of (k+1); $X_1$ represents a divalent linking group having a fluorine atom; $R^{f5}$ represents a hydrogen atom or a monovalent organic group; and k is an integer of 1 to 3, wherein in a case where k is 2 or 3, a plurality of $X_1$s and a plurality of $R^{f5}$s may be each identical or different.

In the above formula (9), examples of the linking group having a valency of (k+1) represented by $R^{f4}$ include a linear or branched hydrocarbon group having 1 to 30 carbon atoms, an alicyclic hydrocarbon group having 3 to 30 carbon atoms, an aromatic hydrocarbon group having 6 to 30 carbon atoms, or a group derived from any of these groups by combining with an oxygen atom, a sulfur atom, an ether group, an ester group, a carbonyl group, an imino group, an amide group or a combination thereof. In addition, the linking group having a valency of (k+1) does not have or has a substituent.

Examples of the linear or branched hydrocarbon group having 1 to 30 carbon atoms include groups derived from any of hydrocarbons such as methane, ethane, propane, butane, pentane, hexane, heptane, decane, icosane and triacontane by removing (k+1) hydrogen atoms therefrom, and the like.

Examples of the alicyclic hydrocarbon group having 3 to 30 carbon atoms include groups derived from any of the following hydrocarbons by removing (k+1) hydrogen atoms therefrom:

monocyclic saturated hydrocarbons such as cyclopropane, cyclobutane, cyclopentane, cyclohexane, cycloheptane, cyclooctane, cyclodecane, methylcyclohexane and ethylcyclohexane;

monocyclic unsaturated hydrocarbons such as cyclobutene, cyclopentene, cyclohexene, cycloheptene, cyclooctene, cyclodecene, cyclopentadiene, cyclohexadiene, cyclooctadiene and cyclodecadiene;

polycyclic saturated hydrocarbons such as bicyclo[2.2.1]heptane, bicyclo[2.2.2]octane, tricyclo[5.2.1.0$^{2,6}$]decane, tricyclo[3.3.1.1$^{3,7}$]decane, tetracyclo[6.2.1.1$^{3,6}$.0$^{2,7}$]dodecane and adamantane;

polycyclic unsaturated hydrocarbons such as bicyclo[2.2.1]heptene, bicyclo[2.2.2]octene, tricyclo[5.2.1.0$^{2,6}$]decene, tricyclo[3.3.1.1$^{3,7}$]decene and tetracyclo[6.2.1.1$^{3,6}$.0$^{2,7}$]dodecene, and the like.

Examples of the aromatic hydrocarbon group having 6 to 30 carbon atoms include groups derived from any of aromatic hydrocarbons such as benzene, naphthalene, phenanthrene, anthracene, tetracene, pentacene, pyrene, picene, toluene, xylene, ethylbenzene, mesitylene and cumene by removing (k+1) hydrogen atoms therefrom, and the like.

In the above formula (9), the divalent linking group having a fluorine atom represented by $X_1$ is exemplified by a divalent linear hydrocarbon group having 1 to 20 carbon atoms and having a fluorine atom. $X_1$ is exemplified by structures represented by the following formulae ($X_1$-1) to ($X_1$-6), and the like.

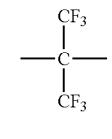

($X_1$-1)

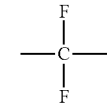

($X_1$-2)

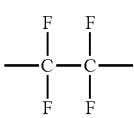

($X_1$-3)

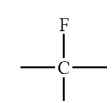

($X_1$-4)

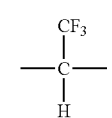

($X_1$-5)

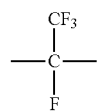

($X_1$-6)

$X_1$ represents preferably a structure represented by the above formulae ($X_1$-1) and ($X_1$-2), and more preferably a structure represented by the formula ($X_1$-2).

In the above formula (9), the monovalent organic group represented by $R^{f5}$ is exemplified by a linear or branched hydrocarbon group having 1 to 30 carbon atoms, an alicyclic hydrocarbon group having 3 to 30 carbon atoms, an aromatic hydrocarbon group having 6 to 30 carbon atoms, or a group derived by combining such a group with an oxygen atom, a sulfur atom, an ether group, an ester group, a carbonyl group, an imino group, an amide group or a combination thereof, and the like.

Examples of the structural unit (f2) include structural units represented by the following formulae (9-1) and (9-2), and the like.

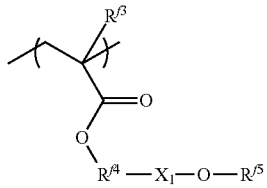

(9-1)

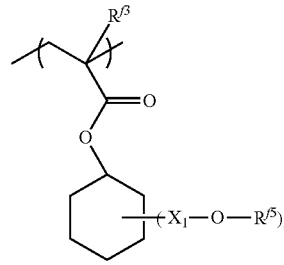

(9-2)

In the above formula (9-1), $R^{f4}$ represents a divalent linear, branched or cyclic saturated or unsaturated hydrocarbon group having 1 to 20 carbon atoms; $R^{f3}$, $X_1$ and $R^{f5}$ is as defined in the above formula (9).

In the above formula (9-2), $R^{f3}$, $X_1$, $R^{f5}$ and k are as defined in the above formula (9), wherein in a case where k is 2 or 3, a plurality of $X_1$s and $R^{f5}$s may be each identical or different.

Examples of the structural units represented by the above formulae (9-1) and (9-2) include structural unite represented by the following formulae (9-1-1) to (9-1-3) and formula (9-2-1), and the like.

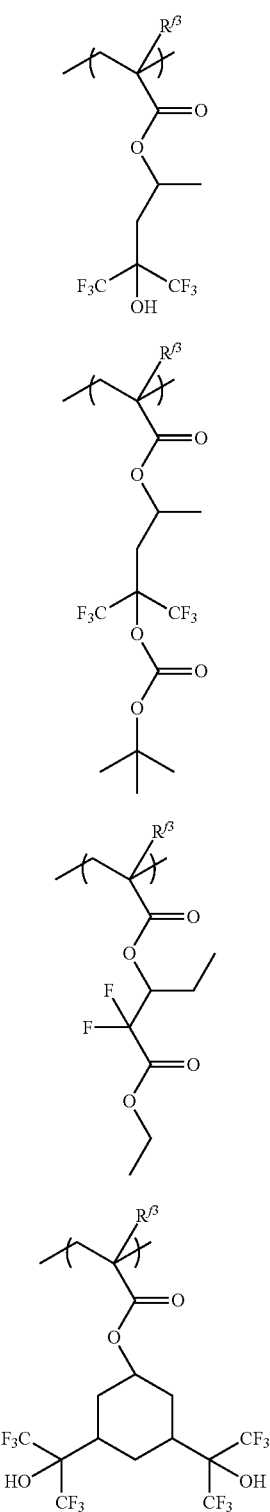

In the above formulae (9-1-1) to (9-1-3) and formula (9-2-1), $R^{\beta}$ is as defined in the above formula (9).

The structural unit (f2) is preferably the structural unit represented by the above formula (9-1), and more preferably the structural unit represented by the above formula (9-1-3).

Examples of the monomer that gives the structural unit (f2) include (meth)acrylic acid [2-(1-ethyloxycarbonyl-1,1-difluoro-n-butyl)] ester, (meth)acrylic acid (1,1,1-trifluoro-2-trifluoromethyl-2-hydroxy-3-propyl) ester, (meth)acrylic acid (1,1,1-trifluoro-2-trifluoromethyl-2-hydroxy-4-butyl) ester, (meth)acrylic acid (1,1,1-trifluoro-2-trifluoromethyl-2-hydroxy-5-pentyl) ester, (meth)acrylic acid 2-{[5-(1',1',1'-trifluoro-2'-trifluoromethyl-2'-hydroxy)propyl]bicyclo[2.2.1]heptyl} ester, and the like. Of these, (meth)acrylic acid [2-(1-ethyloxycarbonyl-1,1-difluoro-n-butyl)] ester is preferred.

The proportion of the structural unit (f2) contained with respect to all the structural units constituting the polymer (F) is preferably 30 mol % to 90 mol %, and more preferably 50 mol % to 80 mol %.

Other Structural Unit

The polymer (F) may have "other structural unit" except for the structural unit (f1) and the structural unit (f2). The other structural unit is exemplified by the structural unit (I) represented by the above formula (7-1) in connection with the polymer (A), and the like.

The proportion of the other structural unit contained with respect to all the structural units constituting the polymer (F) is preferably 5 mol % to 90 mol %, more preferably 10 mol % to 80 mol %, and still more preferably 20 mol % to 70 mol %.

The content of the polymer (F) with respect to 100 parts by mass of the polymer (A) is preferably 0.1 parts by mass to 20 parts by mass, more preferably 1 part by mass to 10 parts by mass, and still more preferably 1 part by mass to 5 parts by mass. When the content is less than 0.1 parts by mass, the effect due to containing the polymer (F) may not be achieved sufficiently. On the other hand, when the content is greater than 20 parts by mass, water repellency of the resist surface becomes so great that a poor development may occur.

The percentage content of fluorine atoms in the polymer (F) is preferably greater than that of the polymer (A). When the percentage content of fluorine atoms in the polymer (F) is greater than that of the polymer (A), water repellency of the surface of a resist film formed using the photoresist composition containing the polymer (A) and the polymer (F) can be enhanced; therefore, it is not necessary to separately provide a resist upper layer film in liquid immersion lithography. In order to sufficiently achieve the effects described above, it is preferred that the difference between the percentage content of fluorine atoms in the polymer (A) and the percentage content of fluorine atoms in the polymer (F) is preferably no less than 1% by mass, and more preferably no less than 3% by mass. It is to be noted that the percentage content of fluorine atoms (% by mass) can be obtained by determining the structure of the polymer by $^{13}$C-NMR, and calculating the percentage content from the results.

Synthesis Method of Polymer (F)

The polymer (F) may be produced by, for example, polymerizing a monomer corresponding to each predetermined structural unit using a radical polymerization initiator in an appropriate solvent.

Examples of the radical polymerization initiator include initiators similar to those used in the synthesis method of the polymer (A), and the like. Examples of the solvent for use in the polymerization include solvents similar to those used in the synthesis method of the polymer (A).

The reaction temperature in the polymerization is typically 40° C. to 150° C., and preferably 50° C. to 120° C. The reaction time period is typically 1 hour to 48 hours, and preferably 1 hour to 24 hours.

The Mw of the polymer (F) is preferably 1,000 to 50,000, more preferably 2,000 to 30,000, and still more preferably 3,000 to 10,000. When the Mw of the polymer (F) is less than 1,000, attaining a sufficient receding contact angle may fail. On the other hand, when the Mw is greater than 50,000, developability when formed into a resist is likely to be impaired.

A ratio (Mw/Mn) of Mw to Mn of the polymer (F) is preferably 1 to 5, and more preferably 1 to 3.

(G) Solvent

The photoresist composition (I) typically contains the solvent (G). The solvent (G) is exemplified by an alcohol solvent, a ketone solvent, an amide solvent, an ether solvent, an ester solvent, and the like. The solvent (G) may be used either alone or in combination of two or more types thereof.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethyl nonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

partially etherified polyhydric alcohol solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether, and the like.

Examples of the ketone solvent include acetone, methyl ethyl ketone, methyl-n-propyl ketone, methyl-n-butyl ketone, diethyl ketone, methyl-iso-butyl ketone, methyl-n-pentyl ketone, ethyl-n-butyl ketone, methyl-n-hexyl ketone, di-iso-butyl ketone, trimethyl nonanone, cyclopentanone, cyclohexanone, cycloheptanone, cyclooctanone, methyl cyclohexanone, 2,4-pentanedione, acetonyl acetone, diacetone alcohol, acetophenone, and the like.

Examples of the amide solvent include N,N'-dimethylimidazolidinone, N-methylformamide, N,N-dimethylformamide, N,N-diethylformamide, acetamide, N-methylacetamide, N,N-dimethylacetamide, N-methylpropionamide, N-methylpyrrolidone, and the like.

Examples of the ether solvent include diethyl ether, dipropyl ether, dibutyl ether, diphenyl ether, and the like.

Examples of the ester solvent include diethyl carbonate, methyl acetate, ethyl acetate, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, diglycol acetate, methoxytriglycol acetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate, diethyl phthalate, and the like.

Of these, the ketone solvent and the ester solvent are preferred. The ketone solvent is more preferably cyclohexanone, and the ester solvent is more preferably propylene glycol monomethyl ether acetate.

(H) Uneven Distribution Accelerator

The uneven distribution accelerator (H) is a component that more efficiently segregates the polymer (F) on the surface of a resist film. When the photoresist composition (I) contains the uneven distribution accelerator (H), the polymer (F) can be segregated on the surface of a resist film, and consequently, the amount of the polymer (F) blended can be decreased. Examples of the uneven distribution accelerator (H) include a lactone compound, a carbonate compound, a nitrile compound, a polyhydric alcohol, and the like. It is to be noted that the uneven distribution accelerator (H) may be used either alone or in combination of two or more types thereof.

Examples of the lactone compound include γ-butyrolactone, valerolactone, mevalonic lactone, norbornane lactone, and the like.

Examples of the carbonate compound include propylene carbonate, ethylene carbonate, butylene carbonate, vinylene carbonate, and the like.

Examples of the nitrile compound include succinonitrile, and the like.

Examples of the polyhydric alcohol include glycerin, and the like.

Of these, the lactone compound is preferred, and γ-butyrolactone is more preferred.

The content of the uneven distribution accelerator (H) with respect to 100 parts by mass of the total amount of the polymer is preferably 5 parts by mass to 300 parts by mass, more preferably 10 mass to 100 parts by mass, and still more preferably 20 parts by mass to 70 parts by mass.

Other Optional Component

The photoresist composition (I) may contain in addition to the components (A) to (H), other optional components such as a surfactant, an alicyclic skeleton-containing compound and a sensitizing agent. The other optional components may be used either alone or in combination of two or more types of each component. Furthermore, the content of the other optional component may be predetermined appropriately depending on the purpose of containing the component.

Preparation of Photoresist Composition (I)

The photoresist composition (I) can be prepared by mixing the polymer (A), the acid diffusion control agent (B), and as needed optional component(s) such as the acid generating agent (C) at a predetermined ratio.

The solid content concentration of the photoresist composition (I) is preferably 0.1% by mass to 50% by mass, more preferably 0.5% by mass to 30% by mass, and still more preferably 1% by mass to 10% by mass.

Photoresist Composition (II)

The photoresist composition (II) according to an embodiment of the present invention contains the polymer (A), and the acid generating agent (D), in which the acid generating agent (D) is a composition containing the compound (I). In addition, the photoresist composition (II) may also contain as a favorable component, the acid diffusion control agent (E). Moreover, the photoresist composition (II) may also contain other optional component(s) such as the solvent (G) within a range not leading to impairment of the effects of the present invention. Hereinafter, each component is explained in detail.

(A) Polymer

The polymer (A) has the structural unit (I). Since the polymer (A) is described in detail in the section of the photoresist composition (I) above, detailed explanation of the polymer (A) for the photoresist composition (II) is omitted.

Structural Unit (I)

The structural unit (I) includes an acid-labile group. The proportion of the structural unit (I) contained with respect to all the structural units constituting the polymer (A) is preferably 5 mol % to 90 mol %, more preferably 5 mol % to 70 mol %, and still more preferably 10 mol % to 60 mol %. When the proportion of the structural unit (I) contained falls within the above range, the shape of the resist pattern after the development can be effectively improved.

Synthesis Method of Polymer (A)

The polymer (A) can be synthesized in accordance with a common method of radical polymerization or the like. Since the synthesis method of the polymer (A) is described above in the section of the Photoresist Composition (I), detailed explanation thereof here is omitted.

The polystyrene equivalent weight average molecular weight (Mw) of the polymer (A) as determined by gel permeation chromatography (GPC) is preferably 1,000 to 50,000, more preferably 1,000 to 40,000, and particularly preferably 1,000 to 30,000. When the Mw of the polymer (A) is less than 1,000, heat resistance as a resist may be deteriorated. On the other hand, when the Mw of the polymer (A) is greater than 50,000, developability as a resist may be impaired.

(D) Acid Generating Agent

The acid generating agent (D) is a radiation-sensitive component that generates an acid upon an exposure. The acid generating agent (D) contains the compound (I). Furthermore, the acid generating agent (D) may contain an acid generating agent other than the compound (I) within a range not leading to impairment of the effects of the present invention. When the photoresist composition (II) contains the acid generating agent (D), diffusion of the acid generating agent (D) per se in the resist film can be inhibited, and consequently leading to an improvement of a contrast between a light-exposed site and a light-unexposed site thereby enabling a resist pattern having a favorable shape to be formed. Since the compound (I) is described above in the section of the Photoresist Compound (I), detailed explanation thereof here is omitted.

Examples of the acid generating agent other than the compound (I) include acid generating agents similar to those exemplified for the acid generating agent (C) in connection with the photoresist composition (I), and the like.

The percentage content of the compound (I) in the acid generating agent (D) is preferably no less than 30% by mass, more preferably no less than 50% by mass, and still more preferably no less than 70% by mass. When the percentage content of the compound (I) falls within the above range, the diffusion of the acid can be more efficiently inhibited.

The content of the acid generating agent (D) with respect to 100 parts by mass of the polymers contained in the photoresist composition (II) is, in light of a securement of sensitivity and developability as a resist, preferably 1 part by mass to 100 parts by mass, more preferably 5 parts by mass to 80 parts by mass, and still more preferably 1 part by mass to 50 parts by mass. When the content of the acid generating agent (D) is less than 1 part by mass, the sensitivity and the developability tend to be deteriorated. On the other hand, when the content is greater than 100 parts by mass, transparency to radioactive rays is decreased, and thus a rectangular resist pattern tends to be hardly obtained.

(E) Acid Diffusion Control Agent

The acid diffusion control agent (E) is a compound that differs from the compound (I). The acid diffusion control agent (E) is a component that controls the diffusion of an acid generated upon an exposure. Due to containing the acid diffusion control agent (E), the photoresist composition (II) enables the diffusion of an acid generated upon an exposure to be inhibited, and consequently the contrast of the resist pattern formed can be improved. The acid diffusion control agent (E) may be used either alone or in combination of two or more types thereof.

Examples of the acid diffusion control agent (E) include an amine compound, an amide group-containing compound, a urea compound, a nitrogen-containing heterocyclic compound, and the like.

Examples of the amine compound include: mono(cyclo)alkylamines; di(cyclo)alkylamines; tri(cyclo)alkylamines; substituted alkylanilines or derivatives thereof; ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis(1-(4-aminophenyl)-1-methylethyl)benzene, 1,3-bis(1-(4-aminophenyl)-1-methylethyl)benzene, bis(2-dimethylaminoethyl) ether, bis(2-diethylaminoethyl) ether, 1-(2-hydroxyethyl)-2-imidazolidinone, 2-quinoxalinol, N,N,N',N'-tetrakis(2-hydroxypropyl)ethylenediamine, N,N,N',N'''N''-pentamethyldiethylenetriamine, and the like.

Examples of the amide group-containing compound include N-t-butoxycarbonyl group-containing amino compounds such as N-t-butoxycarbonyl-4-hydroxypiperidine; N-t-amyloxycarbonyl group-containing amino compounds such as N-t-amyloxycarbonyl-4-hydroxypiperidine; formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine, tris(2-hydroxyethyl) isocyanurate, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include imidazoles such as 2-phenylimidazole; pyridines; piperazines; pyrazine, pyrazole, pyridazine, quinoxaline, purine, pyrrolidine, piperidine, piperidine ethanol, 3-piperidino-1,2-propane diol, morpholine, 4-methylmorpholine, 1-(4-morpholinyl)ethanol, 4-acetyl morpholine, 3-(N-morpholino)-1,2-propane diol, 1,4-dimethyl piperazine, 1,4-diazabicyclo[2.2.2]octane, and the like.

Of these, the amide group-containing compound is preferred, the N-t-butoxycarbonyl group-containing amino compound is more preferred, and N-t-butoxycarbonyl-4-hydroxypiperidine is still more preferred.

The content of the acid diffusion control agent (E) with respect to 100 parts by mass of the total amount of the polymers contained in the photoresist composition (II) is preferably no greater than 30 parts by mass, more preferably no greater than 25 parts by mass, still more preferably no greater than 20 parts by mass, and particularly preferably no greater than 5 parts by mass. When the acid diffusion control agent (E) is contained in excess, the sensitivity of the resist film formed may be significantly decreased.

(G) Solvent

The photoresist composition (II) typically contains the solvent (G). Since the solvent (G) is described above in the section of the Photoresist Composition (I), detailed explanation thereof here is omitted.

Other Optional Components

The photoresist composition (II) may also contain in addition to the components (A) to (G), other optional component(s) such as a surfactant. As the other optional component, those described in connection with the Photoresist Composition (I) above may be employed.

Preparation of Photoresist Composition (II)

The photoresist composition (II) can be prepared by mixing the polymer (A), the acid generating agent (D), and as needed each optional component such as the acid diffusion control agent (E) at a predetermined ratio.

The solid content concentration of the photoresist composition (II) is preferably 0.1% by mass to 50% by mass, more preferably 0.5% by mass to 30% by mass, and still more preferably 1% by mass to 10% by mass.

Method for Forming Resist Pattern

The method for forming the resist pattern in which the photoresist composition is used includes, for example:

(A1) a step of coating the photoresist composition on a substrate to provide a resist film;

(A2) a step of exposing the resist film through a mask; and (A3) a step of developing the exposed resist film.

Hereinafter, each step will be explained.

Step (A1)

In this step, the photoresist composition is coated on a substrate to provide a resist film. The coating method is not particularly limited, and for example, an appropriate coating means such as spin-coating, cast coating or roll coating may be employed. Examples of the substrate include silicon wafer, wafer coated with aluminum, and the like. Specifically, after the composition is coated such that the resulting resist film has a predetermined thickness, prebaking (PB) as needed permits the solvent in the coating film to be volatilized. The film thickness of the coating film is preferably 10 nm to 500 nm. The temperature of PB is typically 60° C. to 140° C., and preferably 80° C. to 120° C. The time period of PB is typically 5 sec to 600 sec, and preferably 10 sec to 300 sec.

Step (A2)

In this step, the resist film provided in the step (A1) (as the case may be, through a liquid immersion medium such as water) is subjected to an exposure by irradiating with a radioactive ray. In this procedure, the irradiation with a radioactive ray is carried out through a mask having a predetermined pattern. The radioactive ray is appropriately selected from, for example, a visible light ray, an ultraviolet ray, a far ultraviolet ray, EUV, an X-ray, an electron beam and the like in accordance with a line width of the intended pattern. Of these, in a case where the photoresist composition (I) is used, a far ultraviolet ray such as an ArF excimer laser beam (wavelength: 193 nm) is preferred, whereas in a case where the photoresist composition (II) is used, an electron beam or EUV light (wavelength: 13.5 nm) is preferred.

Moreover, after the exposure, it is preferred that post exposure baking (PEB) is carried out. When the PEB is carried out, a dissociation reaction of the acid-labile group at an exposed site of the resist film can smoothly proceed. The temperature of PEB is typically 50° C. to 180° C., and preferably 80° C. to 130° C. The time period of PEB is typically 5 sec to 600 sec, and preferably 10 sec to 300 sec.

In the present invention, in order to maximize the potential ability of the photoresist composition, for example, an organic or inorganic antireflective film may be provided on the substrate employed. In addition, in order to prevent influences of basic impurities etc., included in the environment atmosphere, a protective film may be also provided on the coating film, for example. Furthermore, in a case where an exposure by way of liquid immersion is carried out, in order to avoid direct contact of the resist film with the liquid immersion medium, a protective film for liquid immersion may be also provided on the resist film, for example.

Step (A3)

In this step, the resist film exposed in the step (A2) is developed with a developer solution such as e.g., an alkaline developer solution or an organic solvent developer solution to form a predetermined resist pattern.

Examples of the alkaline developer solution include aqueous alkaline solutions prepared by dissolving at least one alkaline compound such as sodium hydroxide, potassium hydroxide, sodium carbonate, sodium silicate, sodium metasilicate, ammonia water, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene or 1,5-diazabicyclo-[4.3.0]-5-nonene.

Examples of the organic solvent developer solution include:

alcohol solvents such as methanol, ethanol, n-propanol, iso-propanol, n-butanol, iso-butanol and sec-butanol;

ether solvents such as diethyl ether, dipropyl ether, dibutyl ether, tetrahydrofuran, dioxane, diphenyl ether and anisole;

ketone solvents such as acetone, methyl ethyl ketone, methyl n-propyl ketone and methyl n-butyl ketone;

amide solvents such as N,N'-dimethylimidazolidinone, N-methylformamide and N,N-dimethylformamide;

ester solvents such as diethyl carbonate, methyl acetate, ethyl acetate, n-propyl acetate, iso-propyl acetate and n-butyl acetate.

These developer solutions may be used either alone or in combination of two or more types thereof. Note that the development is generally followed by washing with water or the like, and drying.

Compound

The compound of another embodiment of the present invention is the compound (I) represented by the above formula (1). This compound is similar to the compound (I) described above (hereinafter, the compound may be also referred to as "compound (I)"). The compound (I) is suitably used as an acid diffusion control agent or an acid generating agent of the photoresist composition. When the compound (I) has the above structure, in a case where the compound (I) is used as an acid diffusion control agent, etc., in the photoresist composition, diffusion thereof in the resist film formed can be inhibited, leading to an improvement of a contrast between a light-exposed site and a light-unexposed site to enable a resist pattern superior in characteristics such as an LWR performance to be formed. Hereinafter, the compound (I) will be explained.

In the above formula (1), $R^1$, $R^2$, $R^3$ and R each independently represent a hydrogen atom or a monovalent organic group having 1 to 20 carbon atoms, wherein two of $R^1$, $R^2$, $R^3$ and R optionally taken together represent a ring structure by binding with each other; X represents a single bond, an oxygen atom or —$NR^a$—, wherein $R^a$ represents a hydrogen atom, a hydroxy group or a monovalent organic group having 1 to 20 carbon atoms, and optionally taken together represents a ring structure by binding with R each other; $A^-$ represents —$SO_3^-$ or —$CO_2^-$; and $M^+$ represents a monovalent onium cation, wherein in a case where $A^-$ represents —$CO_2^-$, at least one of $R^1$, $R^2$, $R^3$ and R does not represent a hydrogen atom.

With respect to details of the formula (1), the explanation is omitted here since the same explanation in the section of the Compound (I) above can be applied thereto.

According to one suitable embodiment of the compound (I), the compound (I) represented by the above formula (1), wherein X represents an oxygen atom, and R is represented by an acid-nonlabile group represented by the above formula (i) (hereinafter, may be also referred to as "compound (I-1)") may be exemplified. When the compound has the above structure, the photoresist composition containing the compound (I-1) as an acid diffusion control agent and/or the like enables a resist pattern more superior in characteristics such as an LWR performance to be formed. This event is presumed to result from improved compatibility owing to similarity of the structure of the compound (I-1) to the structure of a polymer usually contained in the photoresist composition, consequently leading to formation of a uniform resist film.

In the above formula (i), $R^{b1}$, $R^{b2}$ and $R^{b3}$ each independently represent a hydrogen atom, a hydroxy group or a monovalent organic group having 1 to 19 carbon atoms, wherein at least one of the organic group includes at least one of a polar group and a linking group, and the linking group is —O—CO—O—, —S—, —O—, —$SO_2$—O—, —NH— or —CO—O—, and wherein two or more of $R^{b1}$, $R^{b2}$ and $R^{b3}$ optionally taken together represent a ring structure by binding with each other, and at least one of $R^{b1}$, $R^{b2}$ and $R^{b3}$ does not represent a hydrogen atom.

Examples of the monovalent organic group having 1 to 19 carbon atoms which may be represented by $R^{b1}$, $R^{b2}$ and $R^{b3}$ include, among the groups exemplified as the monovalent organic group having 1 to 20 carbon atoms which may be represented by $R^1$, $R^2$, $R^3$ and R in the above formula (1), groups having 1 to 19 carbon atoms, and the like.

Examples of the polar group include a hydroxy group, a cyano group, a sulfo group, a mercapto group, an amino group, a halogen atom, and the like. The halogen atom is preferably a fluorine atom.

The ring structure which may be taken together represented by two or more of $R^{b1}$, $R^{b2}$ and $R^{b3}$ by binding with each other includes aromatic ring structures such as a benzene ring structure and a naphthalene ring structure.

Examples of the compound (I-1) include compounds represented by the above formulae (a-5) to (a-8), (a-22) and (a-29) exemplified as the compound (I), and the like.

According to other suitable embodiment of the compound (I), the compound (I) represented by the above formula (1), wherein X represents an oxygen atom, and R is represented by an acid-labile group represented by the above formula (ii) (hereinafter, may be also referred to as "compound (I-2)") may be exemplified. When the compound (I-2) has the above structure, the photoresist composition containing the compound (I-2) as an acid diffusion control agent and/or the like enables the difference in a rate of dissolution between the light-exposed site and the light-unexposed site to be increased owing to dissociation of the acid-labile group upon an exposure, and as a result, formation of a resist pattern more superior in characteristics such as an LWR performance is enabled.

In the above formula (ii), $R^{c1}$, $R^{c2}$ and $R^{c3}$ each independently represent an alkyl group having 1 to 19 carbon atoms or a monovalent alicyclic hydrocarbon group having 3 to 19 carbon atoms, wherein a part or all of hydrogen atoms included in the alkyl group and the alicyclic hydrocarbon group are unsubstituted or substituted, and wherein two of $R^{c1}$, $R^{c2}$ and $R^{c3}$ optionally taken together represent a divalent alicyclic hydrocarbon group having 3 to 20 carbon atoms by binding with each other together with the carbon atom to which the two of $R^{c1}$, $R^{c2}$ and $R^{c3}$ bond.

Examples of the alkyl group having 1 to 19 carbon atoms represented by $R^{c1}$, $R^{c2}$ and $R^{c3}$ include: linear alkyl groups such as a methyl group, an ethyl group, a n-propyl group and a n-butyl group; branched alkyl groups such as an i-propyl group, an i-butyl group, a sec-butyl group and a t-butyl group; and the like.

Examples of the monovalent alicyclic hydrocarbon group having 3 to 19 carbon atoms which may be represented by $R^{c1}$, $R^{c2}$ and $R^{c3}$, and the divalent alicyclic hydrocarbon group having 3 to 20 carbon atoms which may be taken together represented by two of $R^{c1}$, $R^{c2}$ and $R^{c3}$ by binding with each other together with the carbon atom to which the two f of $R^{c1}$, $R^{c2}$ and $R^{c3}$ bond include: groups having an alicyclic ring derived from norbornane, tricyclodecane, tetracyclododecane or adamantane, or a cycloalkane such as cyclopropane, cyclobutane, cyclopentane, cyclohexane, cycloheptane or cyclooctane; groups obtained by introducing to these groups having an alicyclic ring, a substituent such as e.g., one or more types of or one or more of a linear, branched or cyclic alkyl group having 1 to 4 carbon atoms such as a methyl group, an ethyl group, a n-propyl group, an i-propyl group, a n-butyl group, a 1-methylethyl group, a 1-methylpropyl group, a 2-methylpropyl group and a t-butyl group, and the like.

Examples of the substituent which may substitute for a part or all of hydrogen atoms included in the alkyl group and the alicyclic hydrocarbon group include a hydroxy group, and the like.

Examples of the compound (I-2) include compounds represented by the above formulae (a-9) to (a-12), (a-30) and (a-31) exemplified as the compound (I), and the like.

According to yet other suitable embodiment of the compound (I), the compound (I) represented by the above formula (1) may be exemplified by the compound represented by the above formula (2) (hereinafter, may be also referred to as "compound (I-3)"). When the compound has the above structure, according to the photoresist composition containing the compound (I-3) as an acid diffusion control agent and/or the like, the diffusion of the acid diffusion control agent, etc., in the resist film formed can be further inhibited, leading to an improvement of a contrast between a light-exposed site and a light-unexposed site to enable a resist pattern more superior in characteristics such as an LWR performance to be formed.

In the above formula (2), $A^-$, $M^+$ and $R^a$ are as defined in the above formula (1); and n is an integer of 0 to 5. The integer n is preferably 0 or 1, and more preferably 0.

Examples of the compound (I-3) include compounds represented by the above formulae (b-10) to (b-12) and (b-14) to (b-16) exemplified as the compound (I), and the like.

Production Method of the Compound

Although the production method of the compound is not particularly limited, the compound is preferably produced according to the following method. When the production method of the compound has the steps described below, the compound can be easily and certainly produced.

The production method of the compound (I) includes (1) allowing the compound represented by the above formula (4) to react with NaHSO$_3$, and (2) formula the compound obtained in the step (1) to react with the compound represented by the above formula (5).

In the above formula (4), $R^1$, $R^2$, $R^3$, R and X are as defined in the formula (1). In the above formulae (5) and (6), $M^+$ is as defined in the formula (1). In the above formula (5), $E^-$ represents a monovalent anion.

Examples of the monovalent anion represented by $E^-$ include $HSO_3^-$, and the like. Each step will be explained below.

Step (1)

In this step, the compound represented by the above formula (4) is reacted with NaHSO$_3$. After a material compound such as N-cyclohexylmaleimide as the compound represented by the above formula (4) is added to a solvent such as e.g., water or an alcohol such as methanol, sodium bisulfite (NaHSO$_3$) is further added thereto, and the reaction is allowed while the mixture is stirred with heating. The heating temperature is preferably 30° C. to 150° C., and more preferably 40° C. to 100° C. The heating time period is preferably 30 min to 48 hours, and more preferably 1 hour to 24 hours.

Step (2)

In this step, the compound obtained in the step (1) is reacted with the compound represented by the above formula (5). The compound obtained in the step (1) and a sulfonium salt such as triphenylsulfonium chloride are added to a solvent such as water, and the reaction is allowed while stirring the mixture. The compound represented by the above formula (6) can be synthesized by subsequently extracting the resultant reaction product with an extraction solvent such as dichloromethane, and then drying the extraction liquid. The reaction temperature is preferably 0° C. to 100° C., and more preferably 0° C. to 50° C. The reaction time period is preferably 30 min to 24 hours, and more preferably 1 hour to 12 hours.

EXAMPLES

Hereinafter, the present invention will be explained more specifically by way of Examples, but the present invention is not limited to these Examples. Each measurement in Examples and Comparative Examples was carried out in accordance with the method described below.

Weight Average Molecular Weight (Mw) and Number Average Molecular Weight (Mn)

The Mw and the Mn were determined by gel permeation chromatography (GPC) using GPC columns manufactured by Tosoh Corporation (G2000HXL×2, G3000HXL×1, and G4000HXL×1) under the analytical conditions involving: a flow rate of 1.0 mL/min; an elution solvent of tetrahydrofuran; a sample concentration of 1.0% by mass; an amount of the sample injected of 100 μL: a column temperature of 40° C., with a differential refractometer as a detector, using mono-dispersed polystyrene as a standard. Further, a dispersity index (Mw/Mn) was calculated from the results of the determination of Mw and Mn.

$^{13}$C-NMR Analysis

An analysis was carried out using deuterochloroform as a solvent for measurement with JNM-ECX400 manufactured by JEOL, Ltd., to determine the proportion of each structural unit contained in each polymer (mol %).

Synthesis of Compound (I)

Example 1: Synthesis of Compound (S-1)

After 1.25 g (7.0 mmol) of N-cyclohexylmaleimide (compound (S-1')) as the compound represented by the above formula (4) was added to a 100 mL eggplant-shaped flask charged with 15 mL of methanol and 15 mL of water as a solvent, 0.95 g (9.1 mmol) of sodium bisulfite was further added thereto. Subsequently, the reaction was allowed while stirring the mixture with heating at 55° C. for 18 hours, followed by distillation of the solvent. Then, to the resultant solid matter, 1.46 g (4.9 mmol) of triphenylsulfonium chloride, and 20 mL of dichloromethane and 15 mL of water as a solvent were added, and the reaction was allowed by stirring the mixture at a room temperature for 6 hours. Thereafter, the reaction product thus obtained was extracted using dichloromethane as an extraction solvent, followed by washing with water five times. Then, drying over anhydrous sodium sulfate, followed by distillation of the extraction solvent gave 2.18 g of a compound (S-1) represented by the following formula (yield: 85%).

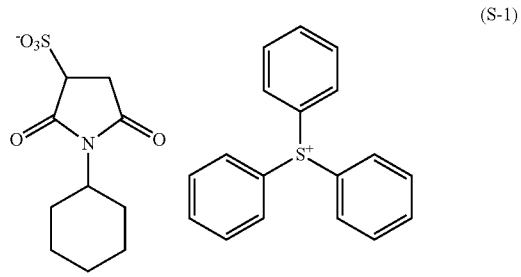

(S-1)

Examples 2 to 43: Synthesis of Compounds (S-2) to (S-43)

Compounds represented by the following formulae (S-2) to (S-43) were synthesized by a similar operation to that of Example 1 except that compounds represented by the following formulae (S-2') to (S-43') were used in place of N-cyclohexylmaleimide (compound (S-1')). It is to be noted that with respect to compounds represented by the following formulae (S-26') and (S-30') to (S-33'), together with the sodium bisulfite, triethylamine as an activator was also added in an amount equivalent to the sodium bisulfite, and then the reaction was allowed while stirring with heating.
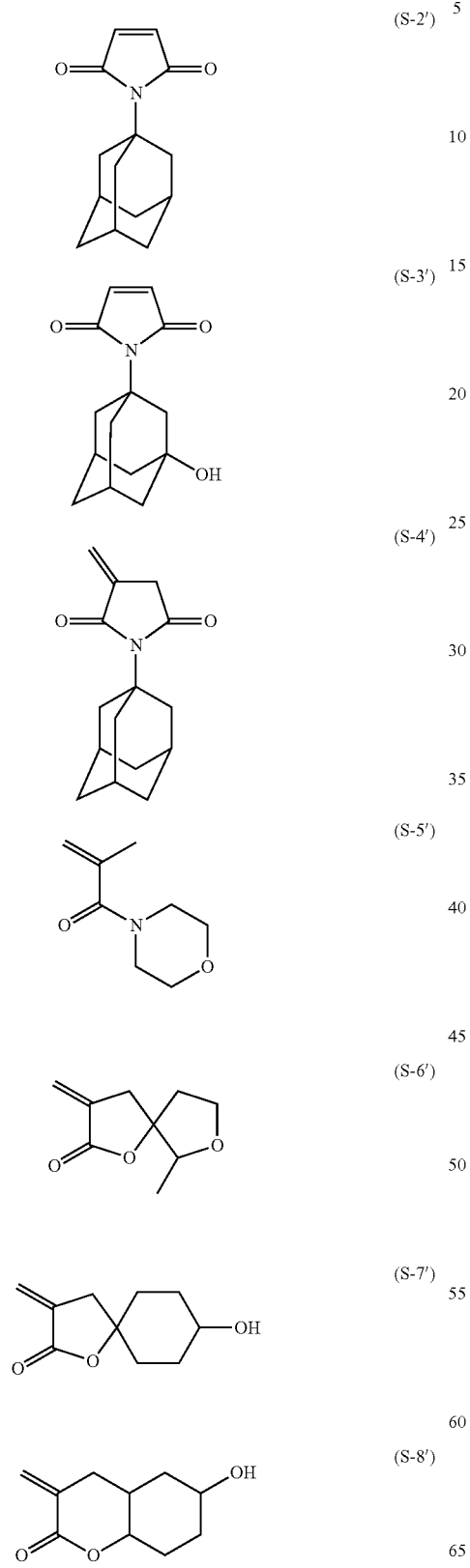
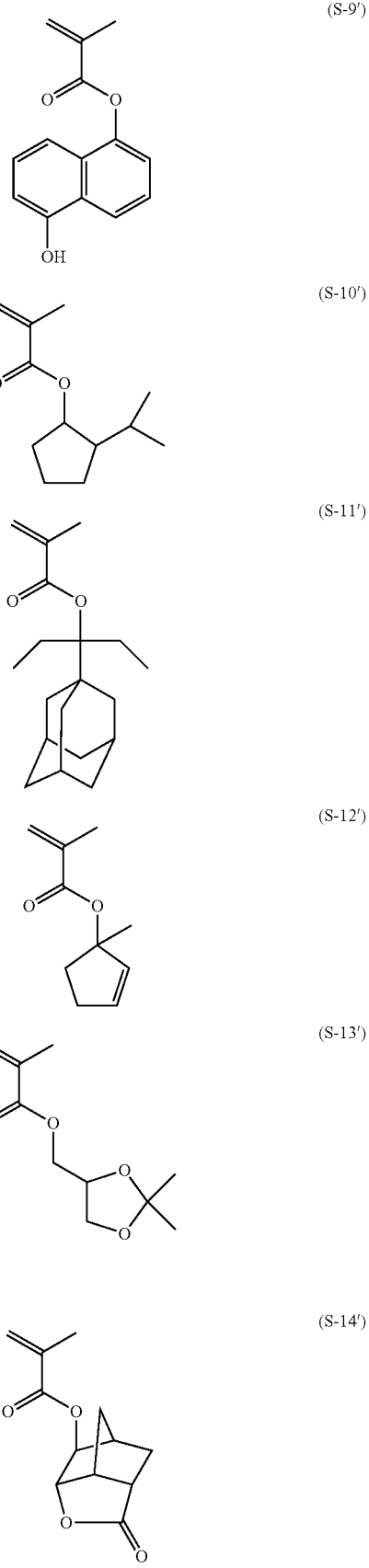

(S-15') 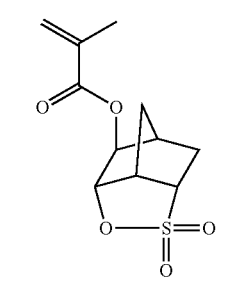
(S-16') 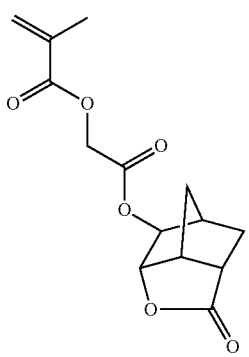
(S-17') 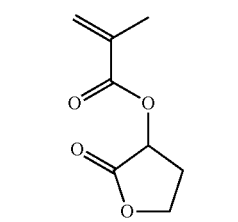
(S-18') 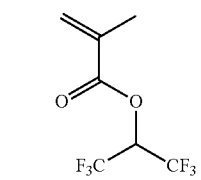
(S-19') 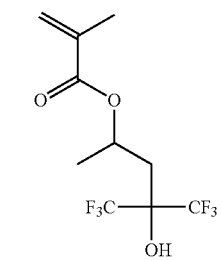
(S-20') 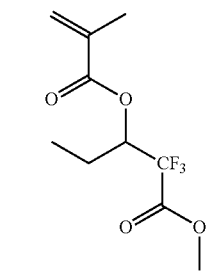
(S-21') 
(S-22') 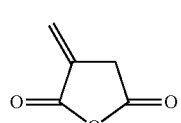
(S-23') 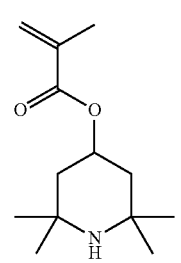
(S-24') 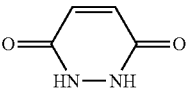
(S-25') 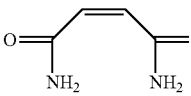
(S-26') 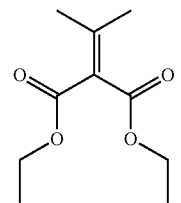
(S-27') 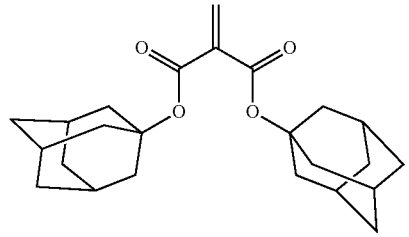
(S-28) 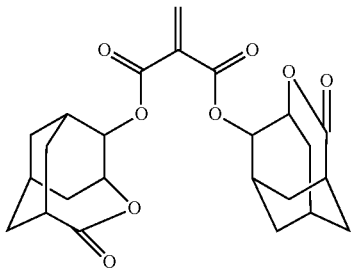
(S-29) 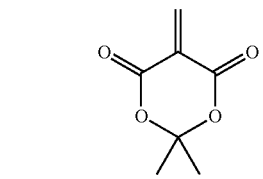

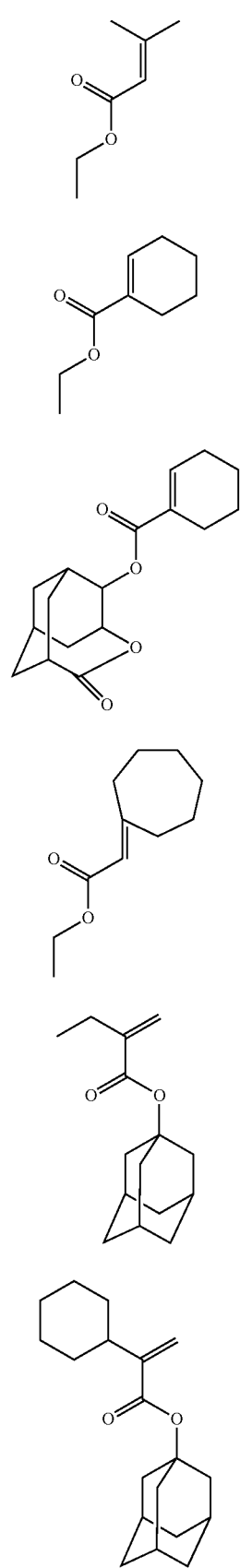
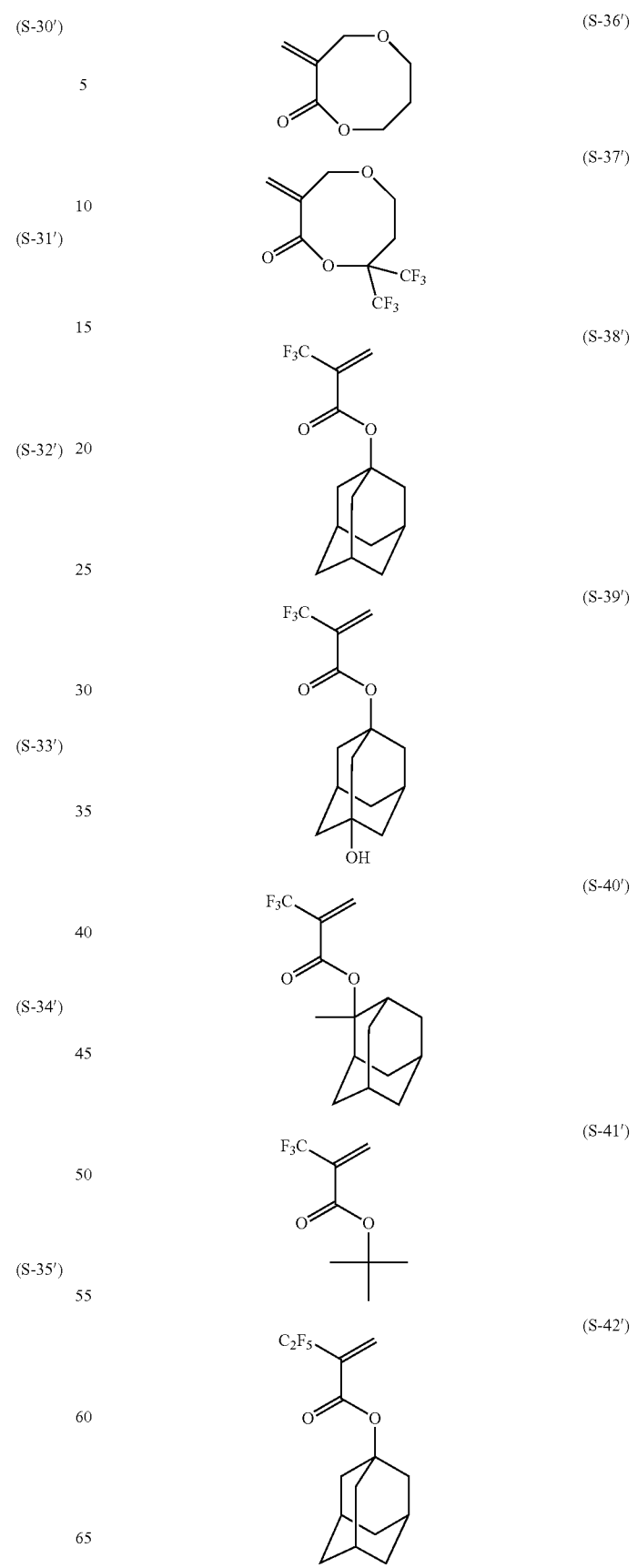

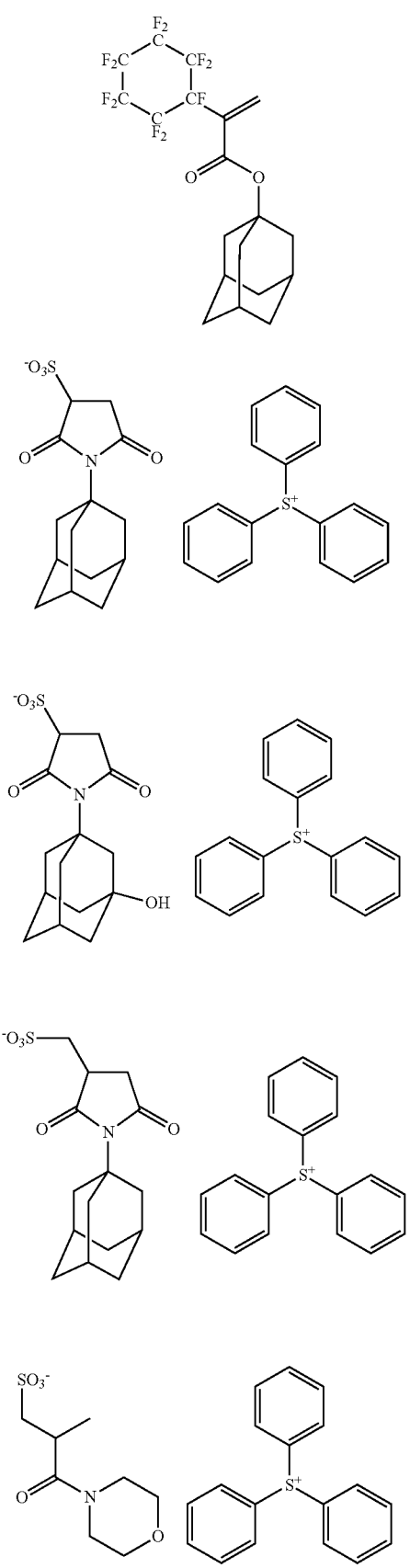
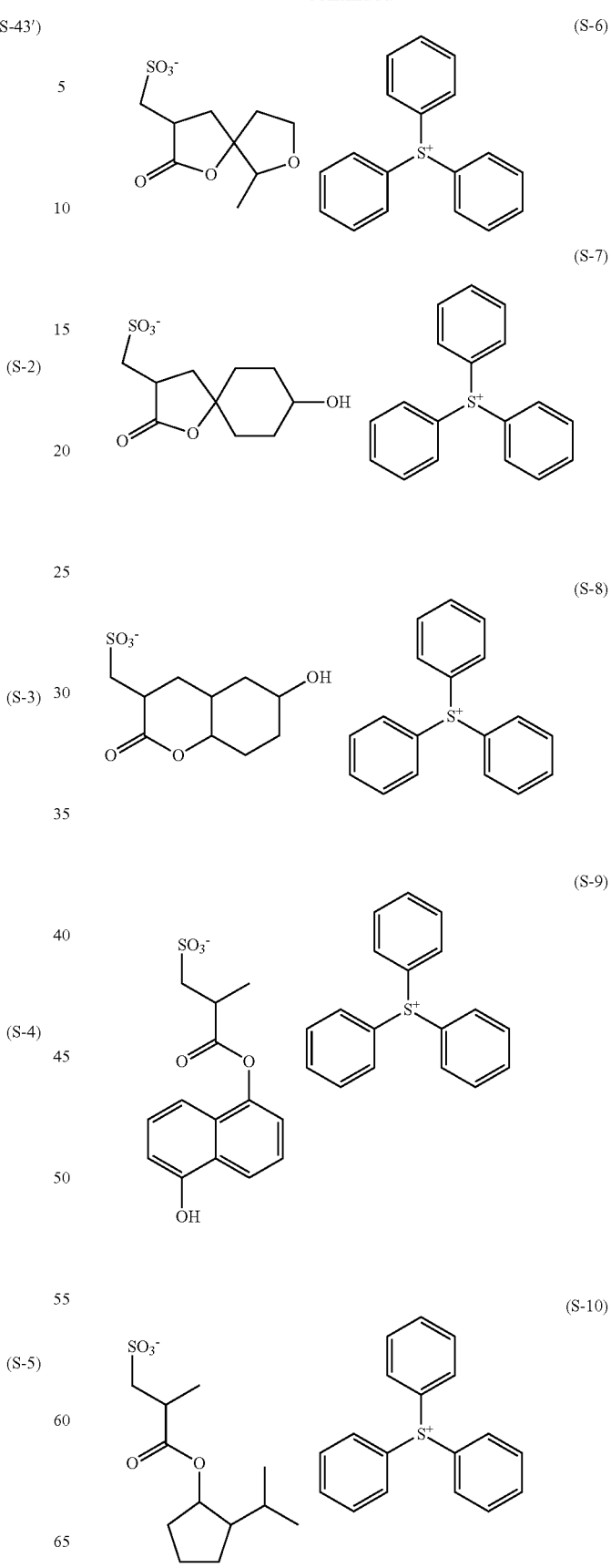

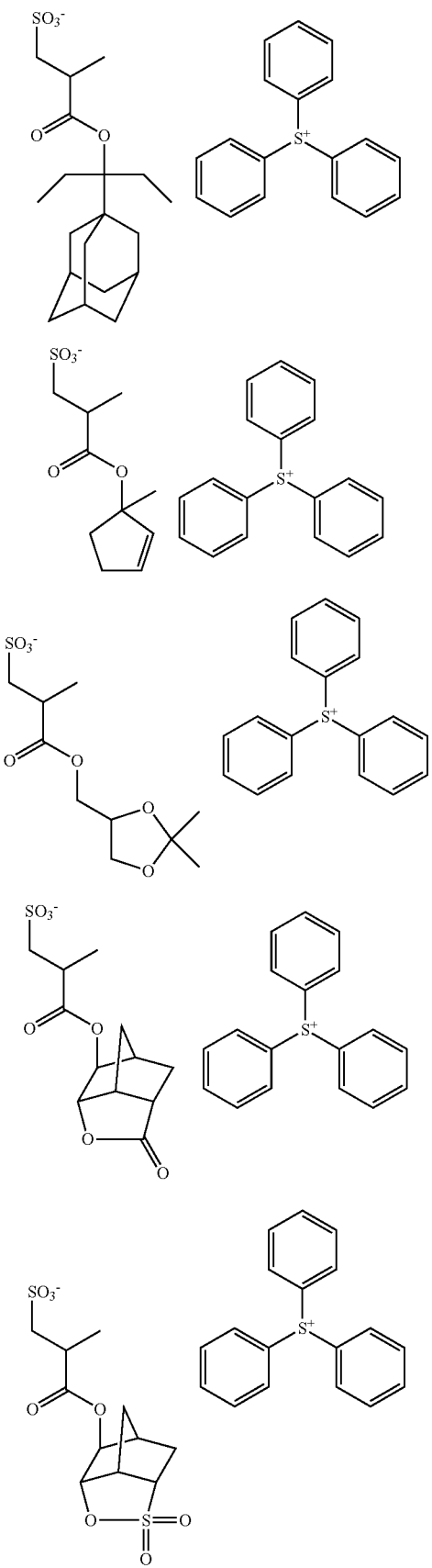

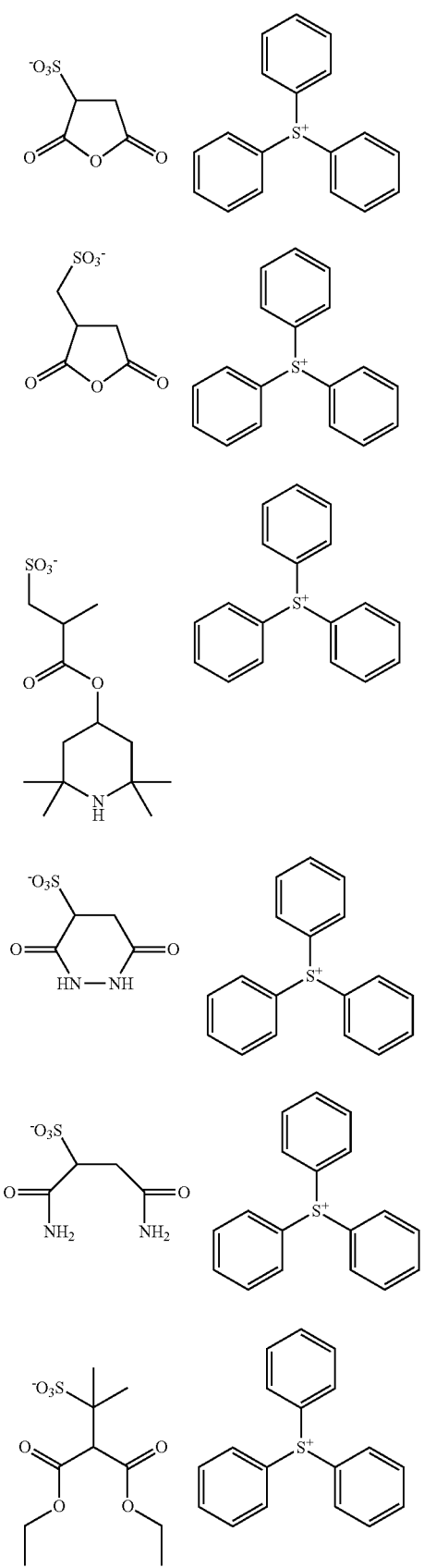
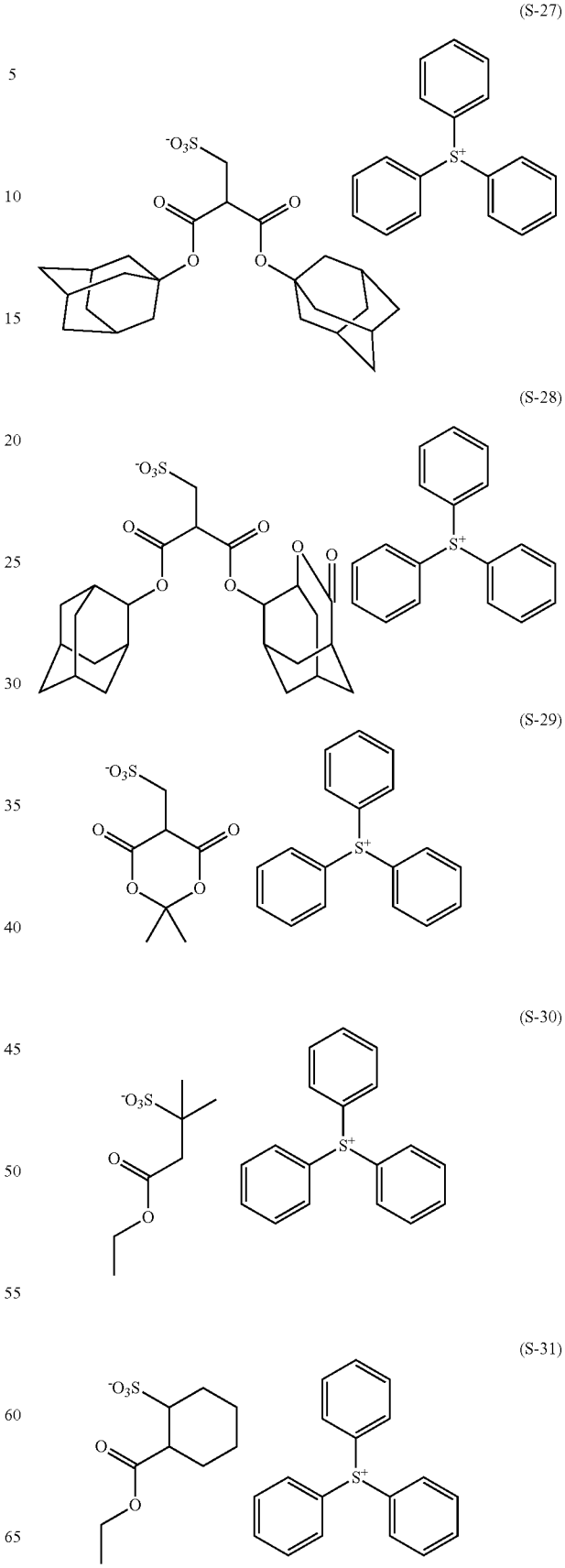

(S-32)
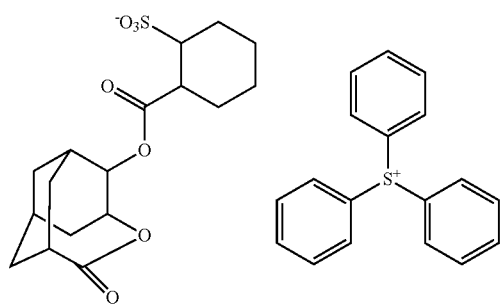
(S-33)
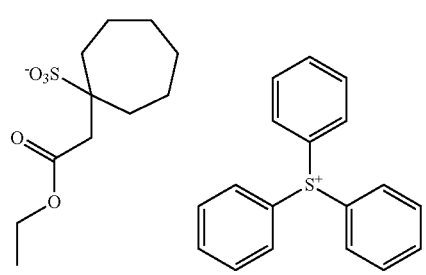
(S-34)
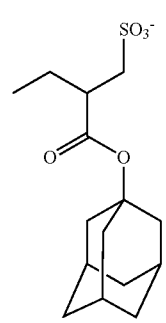
(S-35)
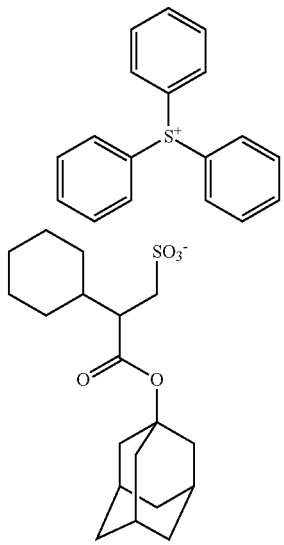
(S-36)
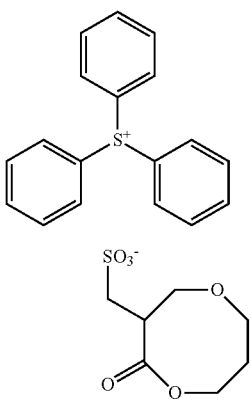
(S-37)
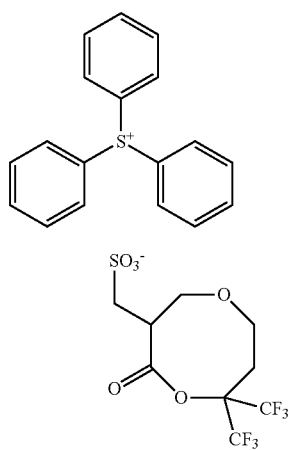

(S-38)
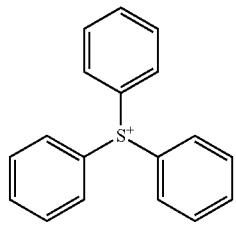
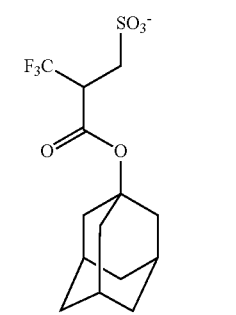
(S-39)
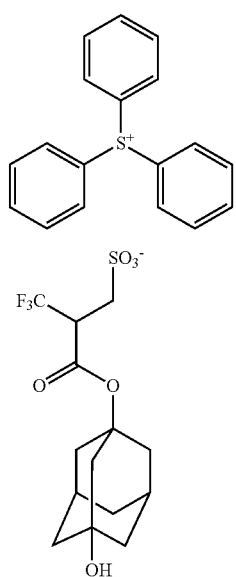
(S-40)
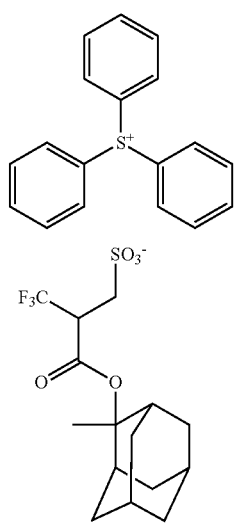
(S-41)
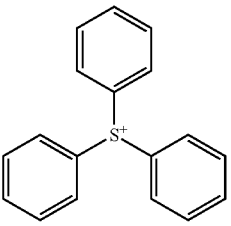
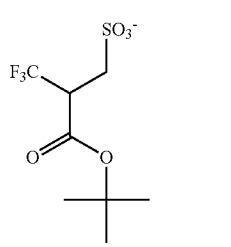
(S-42)
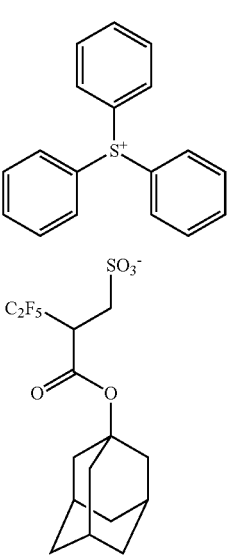
(S-43)
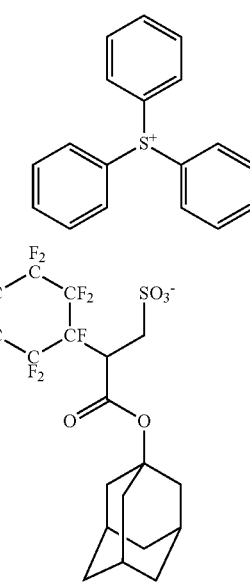

Synthesis of Polymer (A) and Polymer (F)

Monomers used in the synthesis of each polymer in each Example and Comparative Example are shown below.

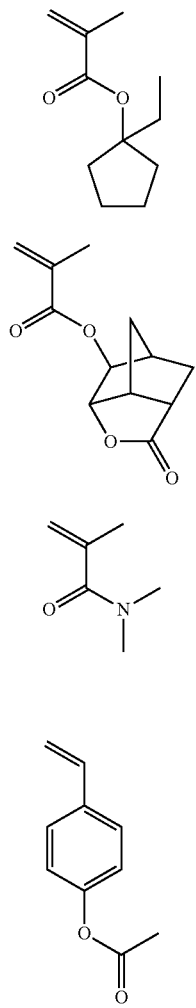
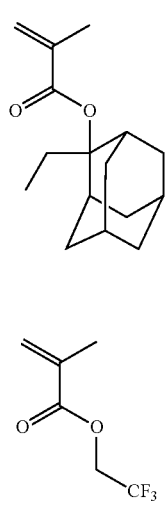
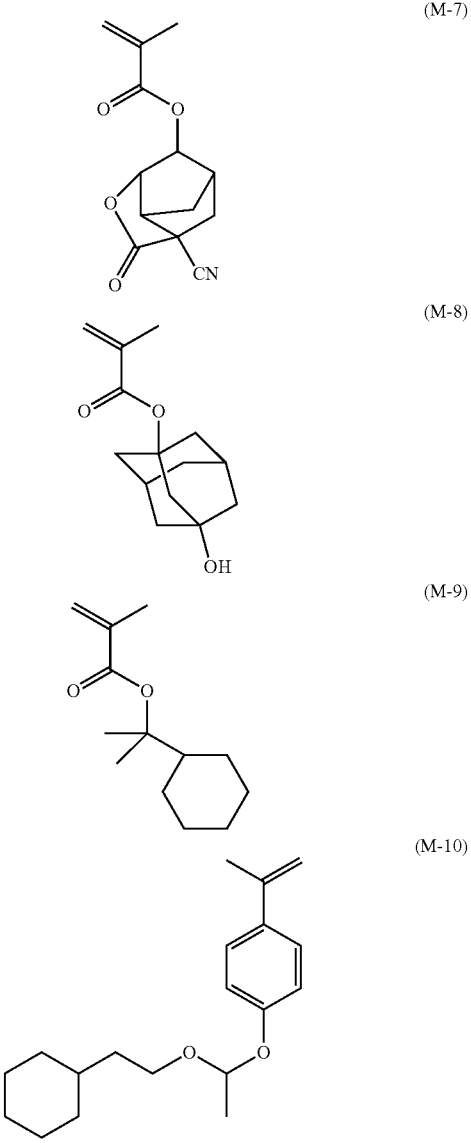

Synthesis Example 1: Synthesis of Polymer (A-1)

A monomer solution was prepared by dissolving 9.01 g (50 mol %) of the compound (M-1) and 10.99 g (50 mol %) of the compound (M-2) in 40 g of 2-butanone, and then adding thereto 0.81 g of AIBN as an initiator. Next, after a 100 mL three-necked flask charged with 20 g of 2-butanone was purged with nitrogen for 30 min, the liquid was heated to 80° C. while stirring, and thereto was added dropwise the monomer solution prepared as described above using a dropping funnel over 3 hours. The time when dropwise addition was started was assumed to be a start time point of the polymerization reaction, and the polymerization reaction was carried out for 6 hours. After completion of the polymerization reaction, the polymerization solution was cooled with water to a temperature of no greater than 30° C. The cooled polymerization solution was charged into 400 g of methanol, and a white powder thus precipitated was filtered off. After the filtered white powder was washed with 80 g of methanol twice, filtration and drying at 50° C. for 17 hours were carried out. Accordingly, a white powdery polymer (A-1) was synthesized (15.6 g; yield: 78%). The polymer (A-1) had an Mw of 7,200, and the Mw/Mn of 1.52. As a result of the $^{13}$C-NMR analysis, the proportions of the structural units derived from (M-1) and (M-2) contained were 50.2 mol % and 49.8 mol %, respectively.

Synthesis Example 2: Synthesis of Polymer (A-2)

A monomer solution was prepared by dissolving 9.53 g (50 mol %) of the compound (M-1), 9.29 g (40 mol %) of the compound (M-2) and 1.18 g (10 mol %) of the compound (M-3) in 40 g of 2-butanone, and then adding thereto 0.86 g of AIBN as an initiator. Next, after a 100 mL three-necked flask charged with 20 g of 2-butanone was purged with nitrogen for 30 min, the liquid was heated to 80° C. while stirring, and thereto was added dropwise the monomer solution prepared as described above using a dropping funnel over 3 hours. The time when dropwise addition was started was assumed to be a start time point of the polymerization reaction, and the polymerization reaction was carried out for 6 hours. After completion of the polymerization reaction, the polymerization solution was cooled with water to a temperature of no greater than 30° C. The cooled polymerization solution was charged into 400 g of methanol, and a white powder thus precipitated was filtered off. After the filtered white powder was washed with 80 g of methanol twice, filtration and drying at 50° C. for 17 hours were carried out. Accordingly, a white powdery polymer (A-2) was synthesized (14.1 g; yield: 71%). The polymer (A-2) had an Mw of 7,100, and the Mw/Mn of 1.53. As a result of the $^{13}$C-NMR analysis, the proportions of the structural units derived from (M-1), (M-2) and (M-3) contained were 50.1 mol %, 40.6 mol % and 9.3 mol %, respectively.

Synthesis Example 3: Synthesis of Polymer (A-3)

After dissolving 55.0 g (65 mol %) of the compound (M-4) and 45.0 g (35 mol %) of the compound (M-5), 4 g of AIBN as an initiator, and 1 g of t-dodecyl mercaptan in 100 g of propylene glycol monomethyl ether, the solution was maintained at a reaction temperature of 70° C. in a nitrogen atmosphere to allow for copolymerization for 16 hours. After completion of the polymerization reaction, the polymerization solution was added dropwise into 1,000 g of n-hexane to permit purification of the polymer through solidification. Next, 150 g of propylene glycol monomethyl ether was again added to the polymer, and thereafter 150 g of methanol, 34 g of triethylamine and 6 g of water were added thereto. A hydrolysis reaction was permitted for 8 hours while refluxing the mixture at a boiling point. After completion of the reaction, the solvent and triethylamine were vacuum-distilled, and the resultant polymer was dissolved in 150 g of acetone. Then, the solution was added dropwise into 2,000 g of water to allow for coagulation, and thus produced white powder was filtered and dried at 50° C. for 17 hours to give a white powdery polymer (A-3) (65.7 g; yield: 76.6%). The polymer (A-3) had an Mw of 10,000, and the Mw/Mn of 2.10. As a result of the $^{13}$C-NMR analysis, the proportions of the structural units derived from p-hydroxystyrene and (M-5) contained were 65.4 mol % and 34.6 mol %, respectively.

Synthesis Example 4: Synthesis of Polymer (A-4)

A monomer solution was prepared by dissolving 7.31 g (40 mol %) of the compound (M-9), 8.59 g (40 mol %) of the compound (M-7) and 4.10 g (20 mol %) of the compound (M-8) in 40 g of 2-butanone, and then adding thereto 0.71 g of AIBN as an initiator. Next, after a 100 mL three-necked flask charged with 20 g of 2-butanone was purged with nitrogen for 30 min, the liquid was heated to 80° C. while stirring, and thereto was added dropwise the monomer solution prepared as described above using a dropping funnel over 3 hours. The time when dropwise addition was started was assumed to be a start time point of the polymerization reaction, and the polymerization reaction was carried out for 6 hours. After completion of the polymerization reaction, the polymerization solution was cooled with water to a temperature of no greater than 30° C. The cooled polymerization solution was charged into 400 g of methanol, and a white powder thus precipitated was filtered off. After the filtered white powder was washed with 80 g of methanol twice, filtration and drying at 50° C. for 17 hours were carried out. Accordingly, a white powdery polymer (A-4) was synthesized (15.0 g; yield: 75%). The polymer (A-4) had an Mw of 7,500, and the Mw/Mn of 1.53. As a result of the $^{13}$C-NMR analysis, the proportions of the structural units derived from (M-9), (M-7) and (M-8) contained were 40.1 mol %, 40.0 mol % and 19.9 mol %, respectively.

Synthesis Example 5: Synthesis of Polymer (A-5)

A monomer solution was prepared by dissolving 7.55 g (40 mol %) of the compound (M-9), 8.87 g (40 mol %) of the compound (M-7), 2.12 g (10 mol %) of the compound (M-8), and 1.46 g (10 mol %) of the compound (M-4) in 40 g of 2-butanone, and then adding thereto 0.86 g of AIBN as an initiator. Next, after a 100 mL three-necked flask charged with 20 g of 2-butanone was purged with nitrogen for 30 min, the liquid was heated to 80° C. while stirring, and thereto was added dropwise the monomer solution prepared as described above using a dropping funnel over 3 hours. The time when dropwise addition was started was assumed to be a start time point of the polymerization reaction, and the polymerization reaction was carried out for 6 hours. After completion of the polymerization reaction, the polymerization solution was cooled with water to a temperature of no greater than 30° C. The cooled polymerization solution was charged into 400 g of methanol, and a white powder thus precipitated was filtered off. Next, 30 g of propylene glycol monomethyl ether was added to the polymer, and thereafter 30 g of methanol, 10 g of triethylamine and 2 g of water were added thereto. A hydrolysis reaction was permitted for 8 hours while refluxing the mixture at a boiling point. After completion of the reaction, the solvent and triethylamine were vacuum-distilled, and the resultant polymer was dissolved in 60 g of 2-butanone. Then, the cooled polymerization solution was charged into 400 g of methanol, and a white powder thus precipitated was filtered off. After the filtered white powder was washed with 80 g of methanol twice, filtration and drying at 50° C. for 17 hours were carried out. Accordingly, a white powdery polymer (A-5) was synthesized (14.4 g; yield: 73%). The polymer (A-5) had an Mw of 7,100, and the Mw/Mn of 1.53. As a result of the $^{13}$C-NMR analysis, the proportions of the structural units derived from (M-9), (M-7) and (M-8), and p-hydroxystyrene contained were 40.1 mol %, 40.1 mol %, 9.9 mol % and 9.9 mol %, respectively.

Synthesis Example 6: Synthesis of Polymer (A-6)

After dissolving 56.7 g (70 mol %) of the compound (M-4) and 43.3 g (30 mol %) of the compound (M-10), 4.1 g of AIBN as an initiator, and 1 g of t-dodecyl mercaptan in 100 g of propylene glycol monomethyl ether, the solution was maintained at a reaction temperature of 70° C. in a nitrogen atmosphere to allow for copolymerization for 16 hours. After completion of the polymerization reaction, the polymerization solution was added dropwise into 1,000 g of n-hexane to permit purification of the polymer through solidification. Next, 150 g of propylene glycol monomethyl ether was again added to the polymer, and thereafter 150 g of methanol, 34 g of triethylamine and 6 g of water were added thereto. A hydrolysis reaction was permitted for 8 hours while refluxing the mixture at a boiling point. After completion of the reaction, the solvent and triethylamine were vacuum-distilled, and the resultant polymer was dissolved in 150 g of acetone. Then, the solution was added dropwise into 2,000 g of water to allow for coagulation, and thus produced white powder was filtered and dried at 50° C. for 17 hours to give a white powder polymer (A-6) (62.1 g; yield: 72.8%). The polymer (A-6) had an Mw of 10,000, and the Mw/Mn of 2.20. As a result of the $^{13}$C-NMR analysis, the proportions of the structural units derived from p-hydroxystyrene and (M-10) contained were 70.2 mol % and 28.8 mol %, respectively.

Synthesis Example 7: Synthesis of Polymer (F-1)

A monomer solution was prepared by dissolving 79.9 g (70 mol %) of the compound (M-1) and 20.91 g (30 mol %) of the compound (M-6) in 100 g of 2-butanone, and then dissolving therein 4.77 g of dimethyl 2,2'-azobisisobutyrate as an initiator. Next, after a 1,000 mL three-necked flask charged with 100 g of 2-butanone was purged with nitrogen for 30 min, the liquid was heated to 80° C. while stirring, and thereto was added dropwise the monomer solution prepared as described above using a dropping funnel over 3 hours. The time when dropwise addition was started was assumed to be a start time point of the polymerization reaction, and the polymerization reaction was carried out for 6 hours. After completion of the polymerization reaction, the polymerization solution was cooled with water to a temperature of no greater than 30° C. After the reaction solution was transferred into a 2 L separatory funnel, the polymerization solution was homogenously diluted with 150 g of n-hexane, and 600 g of methanol was charged thereto followed by mixing.

Subsequently, 30 g of distilled water was charged, and the mixture was stirred for 30 min and left to stand. Thereafter, the underlayer was recovered to obtain a propylene glycol monomethyl ether acetate solution containing a polymer (F-1) in the form of a solid matter (yield: 60%). The polymer (F-1) had an Mw of 7,200, and the Mw/Mn of 2.00. As a result of the $^{13}$C-NMR analysis, the proportions of the structural units derived from (M-1) and (M-6) contained were 71.1 mol % and 28.9 mol %, respectively.

Preparation of Photoresist Composition (I)

The component (B) (other than compounds (S-1) to (S-43)), the acid generating agent (C), the solvent (G) and the uneven distribution accelerator (H) used in preparation of the photoresist compositions (I) of the following Examples 44 to 97 and Comparative Examples 1 and 2 are shown below.

(B) Component
  b-1: triphenylsulfonium 10-camphor-sulfonate
(C) Acid Generating Agent

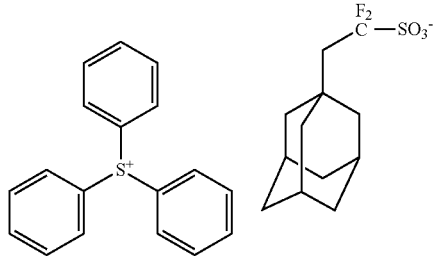
(C-1)

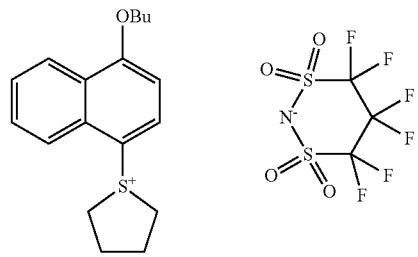
(C-2)

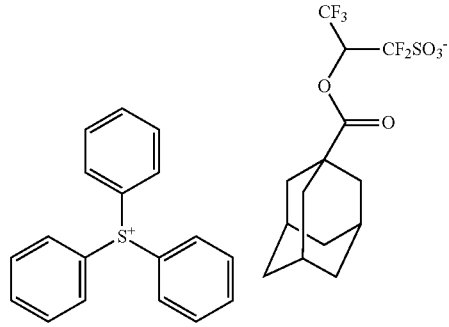
(C-3)

(G) Solvent
  G-1: propylene glycol monomethyl ether acetate
  G-2: cyclohexanone
(H) Uneven Distribution Accelerator
  H-1: γ-butyrolactone Example 44

A photoresist composition (J-1) was prepared by blending 100 parts by mass of (A-1) as the polymer (A), 30 parts by mass of (S-1) as the acid diffusion control agent (B), 8.5 parts by mass of (C-1) as the acid generating agent (C), 3 parts by mass of (F-1) as the polymer (F), 2,240 parts by mass of (G-1) and 960 parts by mass of (G-2) as the solvent (G), and 30 parts by mass of (H-1) as the uneven distribution accelerator (H).

Examples 45 to 97 and Comparative Examples 1 and 2

Each photoresist composition was prepared by a similar operation to that of Example 44 except that each component of the type and in the blend amount shown in Table 1 below was used.

TABLE 1

| | Photoresist composition | (A) Polymer type | blend amount (parts by mass) | (B) Acid diffusion control agent type | blend amount (parts by mass) | (C) Acid generating agent type | blend amount (parts by mass) | (F) Polymer type | blend amount (parts by mass) | (G) Solvent type | blend amount (parts by mass) | (H) Uneven distribution accelerator type | blend amount (parts by mass) |
|---|---|---|---|---|---|---|---|---|---|---|---|---|---|
| Example 44 | J-1 | A-1 | 100 | S-1 | 30 | C-1 | 8.5 | F-1 | 3 | G-1/G-2 | 2,240/960 | H-1 | 30 |
| Example 45 | J-2 | A-1 | 100 | S-1 | 30 | C-2 | 8.5 | F-1 | 3 | G-1/G-2 | 2,240/960 | H-1 | 30 |
| Example 46 | J-3 | A-1 | 100 | S-2 | 30 | C-1 | 8.5 | F-1 | 3 | G-1/G-2 | 2,240/960 | H-1 | 30 |
| Example 47 | J-4 | A-1 | 100 | S-3 | 30 | C-1 | 8.5 | F-1 | 3 | G-1/G-2 | 2,240/960 | H-1 | 30 |
| Example 48 | J-5 | A-1 | 100 | S-4 | 30 | C-1 | 8.5 | F-1 | 3 | G-1/G-2 | 2,240/960 | H-1 | 30 |
| Example 49 | J-6 | A-1 | 100 | S-5 | 30 | C-1 | 8.5 | F-1 | 3 | G-1/G-2 | 2,240/960 | H-1 | 30 |
| Example 50 | J-7 | A-1 | 100 | S-6 | 30 | C-1 | 8.5 | F-1 | 3 | G-1/G-2 | 2,240/960 | H-1 | 30 |
| Example 51 | J-8 | A-1 | 100 | S-7 | 30 | C-1 | 8.5 | F-1 | 3 | G-1/G-2 | 2,240/960 | H-1 | 30 |
| Example 52 | J-9 | A-1 | 100 | S-8 | 30 | C-1 | 8.5 | F-1 | 3 | G-1/G-2 | 2,240/960 | H-1 | 30 |
| Example 53 | J-10 | A-1 | 100 | S-9 | 30 | C-1 | 8.5 | F-1 | 3 | G-1/G-2 | 2,240/960 | H-1 | 30 |
| Example 54 | J-11 | A-1 | 100 | S-10 | 30 | C-1 | 8.5 | F-1 | 3 | G-1/G-2 | 2,240/960 | H-1 | 30 |
| Example 55 | J-12 | A-1 | 100 | S-11 | 30 | C-1 | 8.5 | F-1 | 3 | G-1/G-2 | 2,240/960 | H-1 | 30 |
| Example 56 | J-13 | A-1 | 100 | S-12 | 30 | C-1 | 8.5 | F-1 | 3 | G-1/G-2 | 2,240/960 | H-1 | 30 |
| Example 57 | J-14 | A-1 | 100 | S-13 | 30 | C-1 | 8.5 | F-1 | 3 | G-1/G-2 | 2,240/960 | H-1 | 30 |
| Example 58 | J-15 | A-1 | 100 | S-14 | 30 | C-1 | 8.5 | F-1 | 3 | G-1/G-2 | 2,240/960 | H-1 | 30 |
| Example 59 | J-16 | A-1 | 100 | S-15 | 30 | C-1 | 8.5 | F-1 | 3 | G-1/G-2 | 2,240/960 | H-1 | 30 |
| Example 60 | J-17 | A-1 | 100 | S-16 | 30 | C-1 | 8.5 | F-1 | 3 | G-1/G-2 | 2,240/960 | H-1 | 30 |
| Example 61 | J-18 | A-1 | 100 | S-17 | 30 | C-1 | 8.5 | F-1 | 3 | G-1/G-2 | 2,240/960 | H-1 | 30 |
| Example 62 | J-19 | A-1 | 100 | S-18 | 30 | C-1 | 8.5 | F-1 | 3 | G-1/G-2 | 2,240/960 | H-1 | 30 |
| Example 63 | J-20 | A-1 | 100 | S-19 | 30 | C-1 | 8.5 | F-1 | 3 | G-1/G-2 | 2,240/960 | H-1 | 30 |
| Example 64 | J-21 | A-1 | 100 | S-20 | 30 | C-1 | 8.5 | F-1 | 3 | G-1/G-2 | 2,240/960 | H-1 | 30 |
| Example 65 | J-22 | A-1 | 100 | S-21 | 30 | C-1 | 8.5 | F-1 | 3 | G-1/G-2 | 2,240/960 | H-1 | 30 |
| Example 66 | J-23 | A-1 | 100 | S-22 | 30 | C-1 | 8.5 | F-1 | 3 | G-1/G-2 | 2,240/960 | H-1 | 30 |
| Example 67 | J-24 | A-1 | 100 | S-23 | 30 | C-1 | 8.5 | F-1 | 3 | G-1/G-2 | 2,240/960 | H-1 | 30 |
| Example 68 | J-25 | A-1 | 100 | S-24 | 30 | C-1 | 8.5 | F-1 | 3 | G-1/G-2 | 2,240/960 | H-1 | 30 |
| Example 69 | J-26 | A-1 | 100 | S-25 | 30 | C-1 | 8.5 | F-1 | 3 | G-1/G-2 | 2,240/960 | H-1 | 30 |
| Example 70 | J-27 | A-2 | 100 | S-1 | 30 | C-1 | 8.5 | F-1 | 3 | G-1/G-2 | 2,240/960 | H-1 | 30 |
| Example 71 | J-28 | A-2 | 100 | S-1 | 30 | C-3 | 8.5 | F-1 | 3 | G-1/G-2 | 2,240/960 | H-1 | 30 |
| Example 72 | J-29 | A-2 | 100 | S-2 | 30 | C-1 | 8.5 | F-1 | 3 | G-1/G-2 | 2,240/960 | H-1 | 30 |
| Example 73 | J-30 | A-2 | 100 | S-3 | 30 | C-1 | 8.5 | F-1 | 3 | G-1/G-2 | 2,240/960 | H-1 | 30 |
| Example 74 | J-31 | A-2 | 100 | S-4 | 30 | C-1 | 8.5 | F-1 | 3 | G-1/G-2 | 2,240/960 | H-1 | 30 |
| Example 75 | J-32 | A-2 | 100 | S-5 | 30 | C-1 | 8.5 | F-1 | 3 | G-1/G-2 | 2,240/960 | H-1 | 30 |
| Example 76 | J-33 | A-2 | 100 | S-24 | 30 | C-1 | 8.5 | F-1 | 3 | G-1/G-2 | 2,240/960 | H-1 | 30 |
| Example 77 | J-34 | A-4 | 100 | S-1 | 30 | C-1 | 8.5 | F-1 | 3 | G-1/G-2 | 2,240/960 | H-1 | 30 |
| Example 78 | J-35 | A-4 | 100 | S-7 | 30 | C-1 | 8.5 | F-1 | 3 | G-1/G-2 | 2,240/960 | H-1 | 30 |
| Example 79 | J-36 | A-5 | 100 | S-10 | 30 | C-1 | 8.5 | F-1 | 3 | G-1/G-2 | 2,240/960 | H-1 | 30 |
| Example 80 | J-37 | A-1 | 100 | S-26 | 30 | C-1 | 8.5 | F-1 | 3 | G-1/G-2 | 2,240/960 | H-1 | 30 |
| Example 81 | J-38 | A-1 | 100 | S-27 | 30 | C-1 | 8.5 | F-1 | 3 | G-1/G-2 | 2,240/960 | H-1 | 30 |
| Example 82 | J-39 | A-1 | 100 | S-28 | 30 | C-1 | 8.5 | F-1 | 3 | G-1/G-2 | 2,240/960 | H-1 | 30 |
| Example 83 | J-40 | A-1 | 100 | S-29 | 30 | C-1 | 8.5 | F-1 | 3 | G-1/G-2 | 2,240/960 | H-1 | 30 |
| Example 84 | J-41 | A-1 | 100 | S-30 | 30 | C-1 | 8.5 | F-1 | 3 | G-1/G-2 | 2,240/960 | H-1 | 30 |
| Example 85 | J-42 | A-1 | 100 | S-31 | 30 | C-1 | 8.5 | F-1 | 3 | G-1/G-2 | 2,240/960 | H-1 | 30 |
| Example 86 | J-43 | A-1 | 100 | S-32 | 30 | C-1 | 8.5 | F-1 | 3 | G-1/G-2 | 2,240/960 | H-1 | 30 |
| Example 87 | J-44 | A-1 | 100 | S-33 | 30 | C-1 | 8.5 | F-1 | 3 | G-1/G-2 | 2,240/960 | H-1 | 30 |
| Example 88 | J-45 | A-1 | 100 | S-34 | 30 | C-1 | 8.5 | F-1 | 3 | G-1/G-2 | 2,240/960 | H-1 | 30 |
| Example 89 | J-46 | A-1 | 100 | S-35 | 30 | C-1 | 8.5 | F-1 | 3 | G-1/G-2 | 2,240/960 | H-1 | 30 |
| Example 90 | J-47 | A-1 | 100 | S-36 | 30 | C-1 | 8.5 | F-1 | 3 | G-1/G-2 | 2,240/960 | H-1 | 30 |
| Example 91 | J-48 | A-1 | 100 | S-37 | 30 | C-1 | 8.5 | F-1 | 3 | G-1/G-2 | 2,240/960 | H-1 | 30 |
| Example 92 | J-49 | A-1 | 100 | S-38 | 30 | C-1 | 8.5 | F-1 | 3 | G-1/G-2 | 2,240/960 | H-1 | 30 |
| Example 93 | J-50 | A-1 | 100 | S-39 | 30 | C-1 | 8.5 | F-1 | 3 | G-1/G-2 | 2,240/960 | H-1 | 30 |
| Example 94 | J-51 | A-1 | 100 | S-40 | 30 | C-1 | 8.5 | F-1 | 3 | G-1/G-2 | 2,240/960 | H-1 | 30 |
| Example 95 | J-52 | A-1 | 100 | S-41 | 30 | C-1 | 8.5 | F-1 | 3 | G-1/G-2 | 2,240/960 | H-1 | 30 |
| Example 96 | J-53 | A-1 | 100 | S-42 | 30 | C-1 | 8.5 | F-1 | 3 | G-1/G-2 | 2,240/960 | H-1 | 30 |
| Example 97 | J-54 | A-1 | 100 | S-43 | 30 | C-1 | 8.5 | F-1 | 3 | G-1/G-2 | 2,240/960 | H-1 | 30 |
| Comparative Example 1 | CJ-1 | A-1 | 100 | b-1 | 30 | C-1 | 8.5 | F-1 | 3 | G-1/G-2 | 2,240/960 | H-1 | 30 |
| Comparative Example 2 | CJ-2 | A-2 | 100 | b-1 | 30 | C-1 | 8.5 | F-1 | 3 | G-1/G-2 | 2,240/960 | H-1 | 30 |

Formation of Resist Pattern (1)

An underlayer antireflective film having a film thickness of 105 nm was provided on the surface of a 12 inch silicon wafer by coating an underlayer antireflective film-forming composition (ARC66, manufactured by Brewer Science) with a spin coater (CLEAN TRACK ACT12, manufactured by Tokyo Electron Limited), and heating at 205° C. for 60 sec. On the underlayer antireflective film, each photoresist composition prepared above was coated using the spin coater, and subjected to PB at 90° C. for 60 sec. Thereafter, a resist film having a film thickness of 90 nm was provided through cooling at 23° C. for 30 sec. Next, this resist film was exposed using an ArF excimer laser Immersion Scanner (NSR-S610C, manufactured by NIKON Corporation) under an optical condition involving NA of 1.3, and "dipole" (Sigma: 0.977/0.782), through a mask pattern of 40 nm line-and-space (1L 1S). After the exposure, PEB was carried out at 90° C. for 60 sec. Thereafter, a development with an alkali was carried out using a 2.38% by mass aqueous TMAH solution as an alkaline developer solution, followed by washing with water and drying to form a positive type resist pattern. In forming the resist pattern, an exposure dose at which a line-and-space of 1:1 with a line width of 40 nm was formed through a mask for line-and-space of 1:1 with a target dimension of 40 nm is defined as an "optimum exposure dose".

Formation of Resist Pattern (2)

A negative type resist pattern was formed by a similar operation to that of the above Formation of Resist Pattern (1) except that: n-butyl acetate was used in place of the aqueous TMAH solution to execute the development with an organic solvent; and washing with water was not carried out.

Evaluations

An LWR performance, a resolution, a cross-sectional shape and a depth of focus were evaluated on the resist pattern formed using each of the photoresist compositions in accordance with the following method. The results are shown in Table 2. For measurement of the resist pattern, a scanning electron microscope (S-9380, manufactured by Hitachi High-Technologies Corporation) was used. It is to be noted that "*" in Table 2 indicates a decision standard in each evaluation.

LWR Performance

The resist pattern was observed from above the pattern using the scanning electron microscope described above. The line width was measured at arbitrary points of 50 in total, and a 3 Sigma value was determined from the distribution of the measurements, and the value was defined as an indicative of the LWR performance. The smaller value indicates a better LWR performance. When the value indicting the LWR performance was compared with the value obtained in Comparative Example 1 (i.e., decision standard), the evaluation of the LWR performance was made as favorable "A" in a case where an improvement by no less than 10% was found (i.e., the value of the LWR performance being no greater than 90%), whereas the evaluation was made as unfavorable "B" in a case where an improvement by less than 10% was found (i.e., the value of the LWR performance being greater than 90%).

Resolution

A dimension of the minimum resist pattern which was resolved at the optimum exposure dose was measured, and the measurement result was defined as an indicative of the resolution. The smaller measurement indicates a better resolution. When the obtained measurement was compared with the measurement obtained in Comparative Example 1 (i.e., decision standard), the evaluation of the resolution was made as favorable "A" in a case where an improvement by no less than 10% was found (i.e., the dimension of the minimum resist pattern being no greater than 90%), whereas the evaluation was made as unfavorable "B" in a case where an improvement by less than 10% was found (i.e., the dimension of the minimum resist pattern being greater than 90%).

Cross-Sectional Shape

A cross-sectional shape of the resist pattern which was resolved at the optimum exposure dose was observed to measure a line width Lb at the middle of the resist pattern, and a line width La on the film. In this procedure, in a case where $0.9 \leq La/Lb \leq 1.1$, the cross-sectional shape was evaluated to be favorable "A", whereas in a case where La/Lb does not fall within the above range, the cross-sectional shape was evaluated to be unfavorable "B".

Depth of Focus

On the resist pattern which was resolved at the optimum exposure dose, the dimension when the focus was shifted along the depth direction was observed, and a latitude of the depth direction in which the pattern dimension falls within the range of 90% to 110% of the standard while not accompanied by a bridge and/or residue was measured. The measurement result was defined as the "depth of focus", and the grater measurement indicates more favorable depth of focus. When the obtained measurement was compared with the measurement obtained in Comparative Example 1 (i.e., decision standard), the evaluation of the depth of focus was made as favorable "A" in a case where an improvement by no less than 10% was found (i.e., the depth of focus being no less than 110%), whereas the evaluation was made as unfavorable "B" in a case where an improvement by less than 10% was found (i.e., the depth of focus being less than 110%).

TABLE 2

|  | Development with an alkali | | | | Development with an organic solvent | | | |
| --- | --- | --- | --- | --- | --- | --- | --- | --- |
|  | LWR performance | resolution | cross-sectional shape | depth of focus | LWR performance | resolution | cross-sectional shape | depth of focus |
| Example 44 | A | A | A | A | A | A | A | A |
| Example 45 | A | A | A | A | A | A | A | A |
| Example 46 | A | A | A | A | A | A | A | A |
| Example 47 | A | A | A | A | A | A | A | A |
| Example 48 | A | A | A | A | A | A | A | A |
| Example 49 | A | A | A | A | A | A | A | A |
| Example 50 | A | A | A | A | A | A | A | A |
| Example 51 | A | A | A | A | A | A | A | A |
| Example 52 | A | A | A | A | A | A | A | A |
| Example 53 | A | A | A | A | A | A | A | A |
| Example 54 | A | A | A | A | A | A | A | A |
| Example 55 | A | A | A | A | A | A | A | A |
| Example 56 | A | A | A | A | A | A | A | A |
| Example 57 | A | A | A | A | A | A | A | A |
| Example 58 | A | A | A | A | A | A | A | A |
| Example 59 | A | A | A | A | A | A | A | A |
| Example 60 | A | A | A | A | A | A | A | A |
| Example 61 | A | A | A | A | A | A | A | A |
| Example 62 | A | A | A | A | A | A | A | A |
| Example 63 | A | A | A | A | A | A | A | A |
| Example 64 | A | A | A | A | A | A | A | A |
| Example 65 | A | A | A | A | A | A | A | A |

TABLE 2-continued

|  | Development with an alkali | | | | Development with an organic solvent | | | |
| --- | --- | --- | --- | --- | --- | --- | --- | --- |
|  | LWR performance | resolution | cross-sectional shape | depth of focus | LWR performance | resolution | cross-sectional shape | depth of focus |
| Example 66 | A | A | A | A | A | A | A | A |
| Example 67 | A | A | A | A | A | A | A | A |
| Example 68 | A | A | A | A | A | A | A | A |
| Example 69 | A | A | A | A | A | A | A | A |
| Example 70 | A | A | A | A | A | A | A | A |
| Example 71 | A | A | A | A | A | A | A | A |
| Example 72 | A | A | A | A | A | A | A | A |
| Example 73 | A | A | A | A | A | A | A | A |
| Example 74 | A | A | A | A | A | A | A | A |
| Example 75 | A | A | A | A | A | A | A | A |
| Example 76 | A | A | A | A | A | A | A | A |
| Example 77 | A | A | A | A | A | A | A | A |
| Example 78 | A | A | A | A | A | A | A | A |
| Example 79 | A | A | A | A | A | A | A | A |
| Example 80 | A | A | A | A | A | A | A | A |
| Example 81 | A | A | A | A | A | A | A | A |
| Example 82 | A | A | A | A | A | A | A | A |
| Example 83 | A | A | A | A | A | A | A | A |
| Example 84 | A | A | A | A | A | A | A | A |
| Example 85 | A | A | A | A | A | A | A | A |
| Example 86 | A | A | A | A | A | A | A | A |
| Example 87 | A | A | A | A | A | A | A | A |
| Example 88 | A | A | A | A | A | A | A | A |
| Example 89 | A | A | A | A | A | A | A | A |
| Example 90 | A | A | A | A | A | A | A | A |
| Example 91 | A | A | A | A | A | A | A | A |
| Example 92 | A | A | A | A | A | A | A | A |
| Example 93 | A | A | A | A | A | A | A | A |
| Example 94 | A | A | A | A | A | A | A | A |
| Example 95 | A | A | A | A | A | A | A | A |
| Example 96 | A | A | A | A | A | A | A | A |
| Example 97 | A | A | A | A | A | A | A | A |
| Comparative Example 1 | * | * | B | * | * | * | B | * |
| Comparative Example 2 | B | B | B | B | B | B | B | B |

As is clear from the results shown in Table 2, the LWR performance, the resolution, the cross-sectional shape and the depth of focus were all favorable in any of Examples, whereas each characteristic of the LWR performance, the resolution and the depth of focus in Comparative Example was inferior to that in Example, and the cross-sectional shape was also unfavorable.

Preparation of Photoresist Composition (II)

The component (D) (other than the compound (S-1) to (S-43)), the acid diffusion control agent (E) and the solvent (G) used in the preparation of the photoresist compositions (II) of the following Examples 98 to 141 and Comparative Example 3 are shown below.

(D) Component
  d-1: triphenylsulfonium 2-(adamantan-1-yl)-1,1-difluoroethane-1-sulfonate (E) Acid Diffusion Control Agent
  E-1: N-t-butoxycarbonyl-4-hydroxypiperidine (G) Solvent
  G-1: propylene glycol monomethyl ether acetate
  G-2: cyclohexanone Example 98

A photoresist composition (J-55) was prepared by blending 100 parts by mass of (A-3) as the polymer (A), 20 parts by mass of (S-1) as the acid generating agent (D), 3.6 parts by mass of (E-1) as the acid diffusion control agent (E), and 4,280 parts by mass of (G-1) and 1,830 parts by mass of (G-2) as the solvent (G).

Examples 99 to 141 and Comparative Example 3

Each photoresist composition was prepared by a similar operation to that of Example 98 except that each component of the type and the blend amount shown in Table 3 below was used.

TABLE 3

|  | Photoresist composition | (A) Polymer | | (D) Component | | (E) Acid diffusion control agent | | (G) Solvent | |
| --- | --- | --- | --- | --- | --- | --- | --- | --- | --- |
|  |  | type | blend amount (parts by mass) | type | blend amount (parts by mass) | type | blend amount (parts by mass) | type | blend amount (parts by mass) |
| Example 98 | J-55 | A-3 | 100 | S-1 | 20 | E-1 | 3.6 | G-1/G-2 | 4,280/1,830 |
| Example 99 | J-56 | A-3 | 100 | S-2 | 20 | E-1 | 3.6 | G-1/G-2 | 4,280/1,830 |

TABLE 3-continued

| | Photoresist composition | (A) Polymer type | blend amount (parts by mass) | (D) Component type | blend amount (parts by mass) | (E) Acid diffusion control agent type | blend amount (parts by mass) | (G) Solvent type | blend amount (parts by mass) |
|---|---|---|---|---|---|---|---|---|---|
| Example 100 | J-57 | A-3 | 100 | S-3 | 20 | E-1 | 3.6 | G-1/G-2 | 4,280/1,830 |
| Example 101 | J-58 | A-3 | 100 | S-4 | 20 | E-1 | 3.6 | G-1/G-2 | 4,280/1,830 |
| Example 102 | J-59 | A-3 | 100 | S-5 | 20 | E-1 | 3.6 | G-1/G-2 | 4,280/1,830 |
| Example 103 | J-60 | A-3 | 100 | S-6 | 20 | E-1 | 3.6 | G-1/G-2 | 4,280/1,830 |
| Example 104 | J-61 | A-3 | 100 | S-7 | 20 | E-1 | 3.6 | G-1/G-2 | 4,280/1,830 |
| Example 105 | J-62 | A-3 | 100 | S-8 | 20 | E-1 | 3.6 | G-1/G-2 | 4,280/1,830 |
| Example 106 | J-63 | A-3 | 100 | S-9 | 20 | E-1 | 3.6 | G-1/G-2 | 4,280/1,830 |
| Example 107 | J-64 | A-3 | 100 | S-10 | 20 | E-1 | 3.6 | G-1/G-2 | 4,280/1,830 |
| Example 108 | J-65 | A-3 | 100 | S-11 | 20 | E-1 | 3.6 | G-1/G-2 | 4,280/1,830 |
| Example 109 | J-66 | A-3 | 100 | S-12 | 20 | E-1 | 3.6 | G-1/G-2 | 4,280/1,830 |
| Example 110 | J-67 | A-3 | 100 | S-13 | 20 | E-1 | 3.6 | G-1/G-2 | 4,280/1,830 |
| Example 111 | J-68 | A-3 | 100 | S-14 | 20 | E-1 | 3.6 | G-1/G-2 | 4,280/1,830 |
| Example 112 | J-69 | A-3 | 100 | S-15 | 20 | E-1 | 3.6 | G-1/G-2 | 4,280/1,830 |
| Example 113 | J-70 | A-3 | 100 | S-16 | 20 | E-1 | 3.6 | G-1/G-2 | 4,280/1,830 |
| Example 114 | J-71 | A-3 | 100 | S-17 | 20 | E-1 | 3.6 | G-1/G-2 | 4,280/1,830 |
| Example 115 | J-72 | A-3 | 100 | S-18 | 20 | E-1 | 3.6 | G-1/G-2 | 4,280/1,830 |
| Example 116 | J-73 | A-3 | 100 | S-19 | 20 | E-1 | 3.6 | G-1/G-2 | 4,280/1,830 |
| Example 117 | J-74 | A-3 | 100 | S-20 | 20 | E-1 | 3.6 | G-1/G-2 | 4,280/1,830 |
| Example 118 | J-75 | A-3 | 100 | S-21 | 20 | E-1 | 3.6 | G-1/G-2 | 4,280/1,830 |
| Example 119 | 1-76 | A-3 | 100 | S-22 | 20 | E-1 | 3.6 | G-1/G-2 | 4,280/1,830 |
| Example 120 | J-77 | A-3 | 100 | S-23 | 20 | E-1 | 3.6 | G-1/G-2 | 4,280/1,830 |
| Example 121 | J-78 | A-3 | 100 | S-24 | 20 | E-1 | 3.6 | G-1/G-2 | 4,280/1,830 |
| Example 122 | J-79 | A-3 | 100 | S-25 | 20 | E-1 | 3.6 | G-1/G-2 | 4,280/1,830 |
| Example 123 | J-80 | A-6 | 100 | S-1 | 20 | E-1 | 3.6 | G-1/G-2 | 4,280/1,830 |
| Example 124 | J-81 | A-3 | 100 | S-26 | 20 | E-1 | 3.6 | G-1/G-2 | 4,280/1,830 |
| Example 125 | J-82 | A-3 | 100 | S-27 | 20 | E-1 | 3.6 | G-1/G-2 | 4,280/1,830 |
| Example 126 | J-83 | A-3 | 100 | S-28 | 20 | E-1 | 3.6 | G-1/G-2 | 4,280/1,830 |
| Example 127 | J-84 | A-3 | 100 | S-29 | 20 | E-1 | 3.6 | G-1/G-2 | 4,280/1,830 |
| Example 128 | J-85 | A-3 | 100 | S-30 | 20 | E-1 | 3.6 | G-1/G-2 | 4,280/1,830 |
| Example 129 | J-86 | A-3 | 100 | S-31 | 20 | E-1 | 3.6 | G-1/G-2 | 4,280/1,830 |
| Example 130 | J-87 | A-3 | 100 | S-32 | 20 | E-1 | 3.6 | G-1/G-2 | 4,280/1,830 |
| Example 131 | J-88 | A-3 | 100 | S-33 | 20 | E-1 | 3.6 | G-1/G-2 | 4,280/1,830 |
| Example 132 | J-89 | A-3 | 100 | S-34 | 20 | E-1 | 3.6 | G-1/G-2 | 4,280/1,830 |
| Example 133 | J-90 | A-3 | 100 | S-35 | 20 | E-1 | 3.6 | G-1/G-2 | 4,280/1,830 |
| Example 134 | J-91 | A-3 | 100 | S-36 | 20 | E-1 | 3.6 | G-1/G-2 | 4,280/1,830 |
| Example 135 | J-92 | A-3 | 100 | S-37 | 20 | E-1 | 3.6 | G-1/G-2 | 4,280/1,830 |
| Example 136 | J-93 | A-3 | 100 | S-38 | 20 | E-1 | 3.6 | G-1/G-2 | 4,280/1,830 |
| Example 137 | 3-94 | A-3 | 100 | S-39 | 20 | E-1 | 3.6 | G-1/G-2 | 4,280/1,830 |
| Example 138 | J-95 | A-3 | 100 | S-40 | 20 | E-1 | 3.6 | G-1/G-2 | 4,280/1,830 |
| Example 139 | J-96 | A-3 | 100 | S-41 | 20 | E-1 | 3.6 | G-1/G-2 | 4,280/1,830 |
| Example 140 | J-97 | A-3 | 100 | S-42 | 20 | E-1 | 3.6 | G-1/G-2 | 4,280/1,830 |
| Example 141 | J-98 | A-3 | 100 | S-43 | 20 | E-1 | 3.6 | G-1/G-2 | 4,280/1,830 |
| Comparative Example 3 | CJ-3 | A-3 | 100 | d-1 | 20 | E-1 | 3.6 | G-1/G-2 | 4,280/1,830 |

Formation of Resist Pattern (3)

Each photoresist composition shown in Table 3 was coated on the surface of an 8-inch silicon wafer using a spin coater (CLEAN TRACK ACT8, manufactured by Tokyo Electron Limited), and subjected to PB at 90° C. for 60 sec. Thereafter, a resist film having a film thickness of 50 nm was provided through cooling at 23° C. for 30 sec. Next, this resist film was irradiated with an electron beam using a simplified electron beam writer (manufactured by Hitachi, Ltd., model "HL800D", power: 50 KeV, electric current density: 5.0 A/cm$^2$). After the irradiation, PEB was carried out at 130° C. for 60 sec. Thereafter, a development was carried out using a 2.38% by mass aqueous TMAH solution as an alkaline developer solution at 23° C. for 30 sec, followed by washing with water and drying to form a positive type resist pattern.

Evaluations

An LWR performance, a resolution and a cross-sectional shape were evaluated on the resist pattern formed using each of the photoresist compositions in accordance with the following method. The results are shown in Table 4. For measurement of the resist pattern, a scanning electron microscope (S-9380, manufactured by Hitachi High-Technologies Corporation) was used. It is to be noted that "*" in Table 4 indicates a decision standard in each evaluation.

LWR Performance

The evaluation was made in accordance with a similar method to that of the LWR performance described above except that the decision standard of the LWR performance was the value for Comparative Example 3.

Resolution

A dimension of the minimum resist pattern formed was resolved at the optimum exposure dose was measured, and the measurement result was defined as an indicative of the resolution. The smaller measurement indicates a better resolution. When the obtained measurement was compared with the measurement obtained in Comparative Example 3 (i.e., decision standard), the evaluation of the resolution was made as favorable "A" in a case where an improvement by no less than 10% was found (i.e., the dimension of the minimum resist pattern being no greater than 90%), whereas the evaluation was made as unfavorable "B" in a case where an improvement by less than 10% was found (i.e., the dimension of the minimum resist pattern being greater than 90%).

Cross-Sectional Shape

A cross-sectional shape of the resist pattern formed was observed to measure a line width Lb at the middle of the resist pattern, and a line width La on the film. In this procedure, in a case where 0.9≤La/Lb≤1.1, the cross-sectional shape was evaluated to be favorable "A", whereas in a case where La/Lb does not fall within the above range, the cross-sectional shape was evaluated to be unfavorable "B".

TABLE 4

| | PEB temperature (° C.) | LWR performance | Resolution | Cross-sectional shape |
|---|---|---|---|---|
| Example 98 | 130 | A | A | A |
| Example 99 | 130 | A | A | A |
| Example 100 | 130 | A | A | A |
| Example 101 | 130 | A | A | A |
| Example 102 | 130 | A | A | A |
| Example 103 | 130 | A | A | A |
| Example 104 | 130 | A | A | A |
| Example 105 | 130 | A | A | A |
| Example 106 | 130 | A | A | A |
| Example 107 | 130 | A | A | A |
| Example 108 | 130 | A | A | A |
| Example 109 | 130 | A | A | A |
| Example 110 | 130 | A | A | A |
| Example 111 | 130 | A | A | A |
| Example 112 | 130 | A | A | A |
| Example 113 | 130 | A | A | A |
| Example 114 | 130 | A | A | A |
| Example 115 | 130 | A | A | A |
| Example 116 | 130 | A | A | A |
| Example 117 | 130 | A | A | A |
| Example 118 | 130 | A | A | A |
| Example 119 | 130 | A | A | A |
| Example 120 | 130 | A | A | A |
| Example 121 | 130 | A | A | A |
| Example 122 | 130 | A | A | A |
| Example 123 | 130 | A | A | A |
| Example 124 | 130 | A | A | A |
| Example 125 | 130 | A | A | A |
| Example 126 | 130 | A | A | A |
| Example 127 | 130 | A | A | A |
| Example 128 | 130 | A | A | A |
| Example 129 | 130 | A | A | A |
| Example 130 | 130 | A | A | A |
| Example 131 | 130 | A | A | A |
| Example 132 | 130 | A | A | A |
| Example 133 | 130 | A | A | A |
| Example 134 | 130 | A | A | A |
| Example 135 | 130 | A | A | A |
| Example 136 | 130 | A | A | A |
| Example 137 | 130 | A | A | A |
| Example 138 | 130 | A | A | A |
| Example 139 | 130 | A | A | A |
| Example 140 | 130 | A | A | A |
| Example 141 | 130 | A | A | A |
| Comparative Example 3 | 90 | * | * | B |

As is clear from the results shown in Table 4, the LWR performance, the resolution and the cross-sectional shape were all favorable in any of Examples, whereas each characteristic of the LWR performance and the resolution in Comparative Example was inferior to that in Example, and the cross-sectional shape was also unfavorable.

INDUSTRIAL APPLICABILITY

According to the embodiment of the present invention, there can be provided a photoresist composition capable of leading to an improvement of a contrast between a light-exposed site and a light-unexposed site to enable a resist pattern superior in characteristics such as an LWR performance to be formed. Therefore, the photoresist composition, a compound suited as a basic ingredient of the photoresist composition, and a production method thereof can be suitably used in processes for producing a semiconductor device in which further miniaturization of patterns has been further in progress.

The invention claimed is:

1. A photoresist composition comprising:
a polymer comprising a first structural unit that includes an acid-labile group; and
a first compound represented by formula (1):

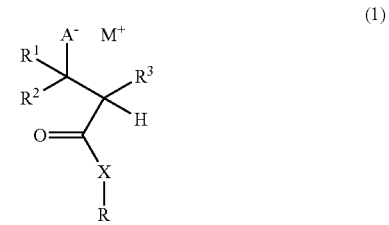

(1)

wherein, in the formula (1), $R^1$ and $R^2$ each independently represent a hydrogen atom or an unsubstituted hydrocarbon group having 1 to 20 carbon atoms, and $R^3$ and R each independently represent a hydrogen atom or a monovalent organic group having 1 to 20 carbon atoms, wherein two of $R^1$, $R^2$, $R^3$ and R optionally taken together represent a ring structure by binding with each other; X represents an oxygen atom or $-NR^a-$, wherein $R^a$ represents a hydrogen atom, a hydroxy group or a monovalent organic group having 1 to 20 carbon atoms; $A^-$ represents $-SO_3^-$ or $-CO_2^-$; and $M^+$ represents a monovalent onium cation, wherein in a case where $A^-$ represents $-CO_2^-$, at least one of $R^1$, $R^2$, $R^3$ and R does not represent a hydrogen atom.

2. The photoresist composition according to claim 1, wherein the first compound represented by the formula (1) is any one of compounds represented by formulae (1-1-1) to (1-1-5), or a mixture of these compounds:

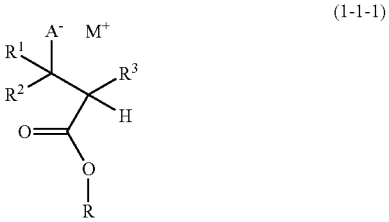

(1-1-1)

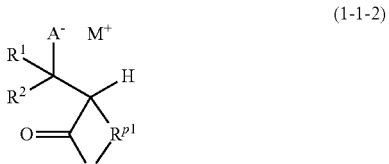

(1-1-2)

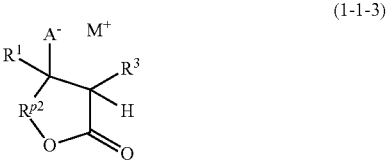

(1-1-3)

-continued

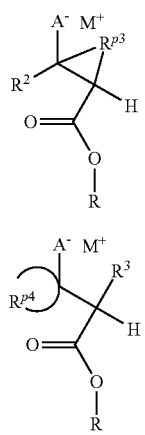
(1-1-4)

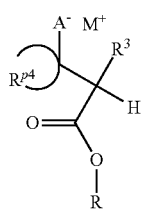
(1-1-5)

wherein, in the formulae (1-1-1) to (1-1-5), $M^+$, $A^-$, $R^1$, $R^2$, $R^3$ and R are as defined in the formula (1); and $R^{p1}$, $R^{p2}$, $R^{p3}$ and $R^{p4}$ each independently represent a divalent organic group.

3. The photoresist composition according to claim 1, wherein the first compound represented by the formula (1) is any one of compounds represented by formulae (1-2-1), (1-2-2), or (1-2-4), or a mixture of these compounds:

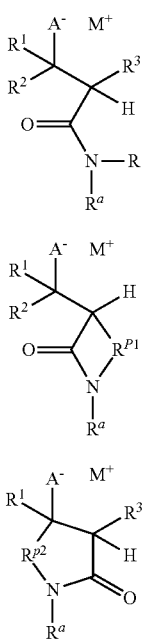
(1-2-1)

(1-2-2)

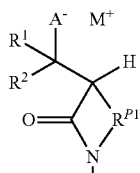
(1-2-4)

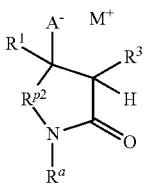

wherein, in the formulae (1-2-1), (1-2-2), and (1-2-4), $M^+$, $A^-$, $R^1$, $R^2$, $R^3$, R and $R^a$ are as defined in the formula (1); and $R^{p1}$ and $R^{p2}$ each independently represent a divalent organic group.

4. The photoresist composition according to claim 1, comprising an acid diffusion control agent, which comprises the first compound.

5. The photoresist composition according to claim 4, wherein the acid-labile group in the first structural unit is polar, or the polymer further comprises a second structural unit represented by formula (3):

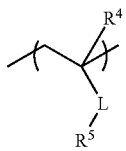
(3)

wherein, in the formula (3), $R^4$ represents a hydrogen atom, a fluorine atom, a methyl group or a trifluoromethyl group; L represents a single bond, —CO—O— or —CO—NH—; and $R^5$ represents an acid-nonlabile group comprising a polar group.

6. The photoresist composition according to claim 4, further comprising an acid generating agent, which differs from the first compound.

7. The photoresist composition according to claim 1 comprising an acid generating agent, which comprises the first compound.

8. The photoresist composition according to claim 7, further comprising an acid diffusion control agent, which differs from the first compound.

9. The photoresist composition according to claim 1, wherein R represents a substituted or unsubstituted monovalent alicyclic hydrocarbon group having 3 to 20 carbon atoms or a substituted or unsubstituted monovalent aromatic hydrocarbon group having 6 to 20 carbon atoms.

10. The photoresist composition according to claim 1, wherein $M^+$ represents a sulfonium cation represented by formula (M') or an iodonium cation represented by formula (M"):

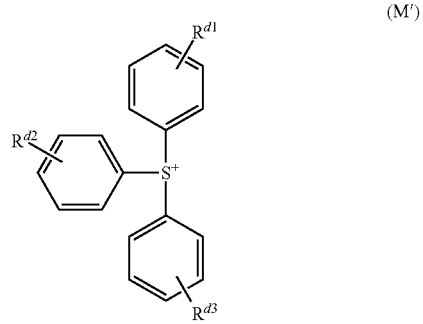
(M')

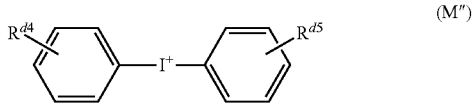
(M")

wherein $R^{d1}$ to $R^{d5}$ each independently represent a hydrogen atom, an alkyl group, an alkoxy group, a hydroxy group or a halogen atom.

11. A compound represented by formula (1):

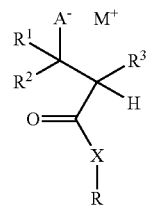
(1)

wherein, in the formula (1), $R^1$ and $R^2$ each independently represent a hydrogen atom or an unsubstituted hydrocarbon group having 1 to 20 carbon atoms, $R^3$ represents a hydrogen atom or a monovalent organic group having 1 to 20 carbon atoms, and R represents a monovalent organic group having 1 to 20 carbon atoms, wherein two of $R^1$, $R^2$, $R^3$ and R optionally taken together represent a ring structure by binding with each other; X represents an oxygen atom or wherein $R^a$ represents a hydroxy group or a monovalent organic group having 1 to 20 carbon atoms; $A^-$ represents $-SO_3^-$ or $-CO_2^-$; and $M^+$ represents a sulfonium cation represented by formula (M') or an iodonium cation represented by formula (M''):

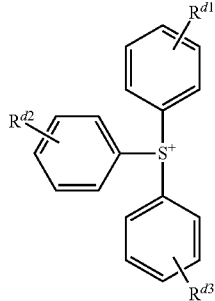

(M')

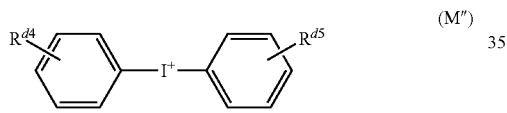

(M'')

wherein $R^{d1}$ to $R^{d5}$ each independently represent a hydrogen atom, an alkyl group, an alkoxy group, a hydroxy group or a halogen atom.

12. The compound according to claim 11, wherein in the formula (1), X represents an oxygen atom, and R is an acid-nonlabile group represented by formula (i):

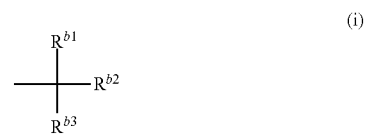

(i)

wherein, in the formula (i), $R^{b1}$, $R^{b2}$ and $R^{b3}$ each independently represent a hydrogen atom, a hydroxy group or a monovalent organic group having 1 to 19 carbon atom, wherein at least one of the monovalent organic group comprises at least one of a polar group and a linking group, and the linking group is $-O-CO-O-$, $-S-$, $-O-$, $-SO_2-O-$, $-NH-$ or $-CO-O-$, and wherein two or more of $R^{b1}$, $R^{b2}$ and $R^{b3}$ optionally taken together represent a ring structure by binding with each other, and at least one of $R^{b1}$, $R^{b2}$ and $R^{b3}$ does not represent a hydrogen atom.

13. The compound according to claim 11, wherein in the formula (1), X represents an oxygen atom, and R is an acid-labile group represented by formula (ii):

(ii)

wherein, in the formula (ii), $R^{c1}$, $R^{c2}$ and $R^{c3}$ each independently represent an alkyl group having 1 to 19 carbon atoms or a monovalent alicyclic hydrocarbon group having 3 to 19 carbon atoms, wherein a part or all of hydrogen atoms included in the alkyl group and the alicyclic hydrocarbon group are unsubstituted or substituted, and wherein two of $R^{c1}$, $R^{c2}$ and $R^{c3}$ optionally taken together represent a divalent alicyclic hydrocarbon group having 3 to 20 carbon atoms by binding with each other together with the carbon atom to which the two of $R^{c1}$, $R^{c2}$ and $R^{c3}$ bond.

14. The compound according to claim 11, wherein R represents a substituted or unsubstituted monovalent alicyclic hydrocarbon group having 3 to 20 carbon atoms or a substituted or unsubstituted monovalent aromatic hydrocarbon group having 6 to 20 carbon atoms.

* * * * *

UNITED STATES PATENT AND TRADEMARK OFFICE
CERTIFICATE OF CORRECTION

PATENT NO. : 9,720,322 B2  
APPLICATION NO. : 15/252553  
DATED : August 1, 2017  
INVENTOR(S) : Hayato Namai et al.

It is certified that error appears in the above-identified patent and that said Letters Patent is hereby corrected as shown below:

Claim 11, Column 83, Line 9 "an oxygen atom or wherein" should read -- an oxygen atom or $-NR^a-$, wherein --.

Signed and Sealed this  
Tenth Day of April, 2018

Andrei Iancu  
*Director of the United States Patent and Trademark Office*